(12) United States Patent
Pilla et al.

(10) Patent No.: US 8,415,123 B2
(45) Date of Patent: *Apr. 9, 2013

(54) ELECTROMAGNETIC TREATMENT APPARATUS AND METHOD FOR ANGIOGENESIS MODULATION OF LIVING TISSUES AND CELLS

(75) Inventors: Arthur A. Pilla, Oakland, NJ (US); Andre' A. DiMino, Woodcliff Lake, NJ (US)

(73) Assignee: Ivivi Health Sciences, LLC, San Francisco, CA (US)

( * ) Notice: Subject to any disclaimer, the term of this patent is extended or adjusted under 35 U.S.C. 154(b) by 273 days.

This patent is subject to a terminal disclaimer.

(21) Appl. No.: 12/661,377

(22) Filed: Mar. 15, 2010

(65) Prior Publication Data

US 2010/0179373 A1 Jul. 15, 2010

Related U.S. Application Data

(62) Division of application No. 11/110,000, filed on Apr. 19, 2005, now abandoned.

(60) Provisional application No. 60/563,104, filed on Apr. 19, 2004.

(51) Int. Cl.
*A61N 1/06* (2006.01)

(52) U.S. Cl. .......................... 435/173.1; 600/10; 600/14

(58) Field of Classification Search .................. None
See application file for complete search history.

(56) References Cited

U.S. PATENT DOCUMENTS

| | | | |
|---|---|---|---|
| 1,233,841 A | 7/1917 | Butcher |
| 2,130,758 A | 9/1938 | Rose |
| 2,276,996 A | 3/1942 | Milinowski |
| 2,648,727 A | 8/1953 | Rockwell |
| 3,043,310 A | 7/1962 | Milinowski |
| 3,181,535 A | 5/1965 | Milinowski |
| 3,270,746 A | 9/1966 | Kendall et al. |
| 3,329,148 A | 7/1967 | Kendall |
| 3,329,149 A | 7/1967 | Kendall et al. |
| 3,800,802 A | 4/1974 | Berry et al. |
| 3,890,953 A | 6/1975 | Kraus et al. |
| 3,952,751 A | 4/1976 | Yarger |
| 3,978,864 A | 9/1976 | Smith |
| 4,028,518 A | 6/1977 | Boudouris et al. |
| 4,105,017 A | 8/1978 | Ryaby et al. |
| 4,197,851 A | 4/1980 | Fellus |
| 4,266,532 A | 5/1981 | Ryaby et al. |
| 4,305,115 A | 12/1981 | Armitage |
| 4,315,503 A | 2/1982 | Ryaby et al. |
| 4,338,945 A | 7/1982 | Kosugi et al. |
| 4,374,482 A | 2/1983 | Moore et al. |
| 4,454,882 A | 6/1984 | Takano |
| 4,616,629 A | 10/1986 | Moore |
| 4,627,438 A | 12/1986 | Liss et al. |
| 4,654,574 A | 3/1987 | Thaler |
| 4,672,951 A | 6/1987 | Welch |
| 4,674,482 A | 6/1987 | Waltonen et al. |
| 4,793,325 A | 12/1988 | Cadossi et al. |
| 4,829,984 A | 5/1989 | Gordon |
| 4,889,526 A | 12/1989 | Rauscher et al. |
| 4,926,881 A | 5/1990 | Ichinomiya et al. |
| 4,993,413 A | 2/1991 | McLeod et al. |
| 4,998,532 A | 3/1991 | Griffith |
| 5,000,178 A | 3/1991 | Griffith |
| 5,014,699 A | 5/1991 | Pollack et al. |
| 5,123,898 A | 6/1992 | Liboff et al. |
| 5,181,902 A | 1/1993 | Erickson et al. |
| 5,224,922 A | 7/1993 | Kurtz |
| 5,338,286 A | 8/1994 | Abbott et al. |
| 5,370,680 A | 12/1994 | Proctor |
| 5,386,837 A | 2/1995 | Sterzer |
| 5,407,421 A | 4/1995 | Goldsmith |
| 5,478,303 A | 12/1995 | Foley-Nolan et al. |
| 5,480,373 A | 1/1996 | Fischer et al. |
| 5,518,496 A | 5/1996 | McLeod et al. |
| 5,584,863 A | 12/1996 | Rauch et al. |
| 5,718,246 A | 2/1998 | Vona |
| 5,718,721 A | 2/1998 | Ross |
| 5,723,001 A | 3/1998 | Pilla et al. |
| 5,743,844 A | 4/1998 | Tepper et al. |

(Continued)

FOREIGN PATENT DOCUMENTS

| | | |
|---|---|---|
| CA | 0608693 | 11/1960 |
| CN | 1052053 A | 6/1991 |

(Continued)

OTHER PUBLICATIONS

Albensi et al.; Diffusion and high resolution MRI of traumatic brain injury in rats: time course and correlation with histology. Exp Neurol 162, 61-72 (Mar. 2000).

(Continued)

*Primary Examiner* — Jim Ketter
(74) *Attorney, Agent, or Firm* — Shay Glenn LLP

(57) ABSTRACT

An apparatus and method for electromagnetic treatment of living tissues and cells comprising: configuring at least one waveform according to a mathematical model having at least one waveform parameter, said at least one waveform to be coupled to a angiogenesis and neovascularization target pathway structure; choosing a value of said at least one waveform parameter so that said at least waveform is configured to be detectable in said angiogenesis and neovascularization target pathway structure above background activity in said target pathway structure; generating an electromagnetic signal from said configured at least one waveform; and coupling said electromagnetic signal to said angiogenesis and neovascularization target pathway structure using a coupling device.

24 Claims, 4 Drawing Sheets

U.S. PATENT DOCUMENTS

| | | |
|---|---|---|
| 5,778,894 A | 7/1998 | Dorogi et al. |
| 5,792,209 A | 8/1998 | Varner et al. |
| 5,814,078 A | 9/1998 | Zhou et al. |
| 5,877,627 A | 3/1999 | Fischer et al. |
| 5,908,444 A | 6/1999 | Azure |
| 5,951,459 A | 9/1999 | Blackwell |
| 5,968,527 A | 10/1999 | Litovitz |
| 5,990,177 A | 11/1999 | Brown |
| 5,997,464 A | 12/1999 | Blackwell |
| 6,004,257 A | 12/1999 | Jacobson |
| 6,083,149 A | 7/2000 | Wascher et al. |
| 6,086,525 A | 7/2000 | Davey et al. |
| 6,099,459 A | 8/2000 | Jacobson |
| 6,132,362 A | 10/2000 | Tepper et al. |
| 6,149,577 A | 11/2000 | Bouldin et al. |
| 6,155,966 A | 12/2000 | Parker |
| 6,190,893 B1 | 2/2001 | Shastri et al. |
| 6,200,259 B1 | 3/2001 | March |
| 6,213,934 B1 | 4/2001 | Bianco et al. |
| 6,231,528 B1 | 5/2001 | Kaufman et al. |
| 6,234,953 B1 | 5/2001 | Thomas et al. |
| 6,246,912 B1 | 6/2001 | Sluijter et al. |
| 6,261,221 B1 | 7/2001 | Tepper et al. |
| 6,261,831 B1 | 7/2001 | Agee |
| 6,301,506 B1 | 10/2001 | den Boer et al. |
| 6,321,120 B1 | 11/2001 | Surbeck et al. |
| 6,334,069 B1 | 12/2001 | George et al. |
| 6,418,345 B1 | 7/2002 | Tepper et al. |
| 6,421,562 B1 | 7/2002 | Ross |
| 6,424,863 B1 | 7/2002 | Flock et al. |
| 6,434,426 B1 | 8/2002 | Munneke et al. |
| 6,443,883 B1 | 9/2002 | Ostrow et al. |
| 6,458,151 B1 | 10/2002 | Saltiel |
| 6,458,157 B1 | 10/2002 | Suaning et al. |
| 6,463,336 B1 | 10/2002 | Mawhinney |
| 6,556,872 B2 | 4/2003 | Hauck |
| 6,560,489 B2 | 5/2003 | Hauck |
| 6,561,968 B1 | 5/2003 | Dissing et al. |
| 6,569,654 B2 | 5/2003 | Shastri et al. |
| 6,589,159 B2 | 7/2003 | Paturu |
| 6,629,971 B2 | 10/2003 | McDaniel |
| 6,648,812 B2 | 11/2003 | Ardizzone |
| 6,675,047 B1 | 1/2004 | Konoplev et al. |
| 6,678,562 B1 | 1/2004 | Tepper et al. |
| 6,684,108 B2 | 1/2004 | Surbeck et al. |
| 6,701,185 B2 | 3/2004 | Burnett et al. |
| 6,839,589 B2 | 1/2005 | Petlan |
| 6,844,378 B1 | 1/2005 | Martin et al. |
| 6,919,205 B2 | 7/2005 | Brighton |
| 6,934,580 B1 | 8/2005 | Osorio et al. |
| 6,955,642 B1 | 10/2005 | Simon |
| 7,010,353 B2 | 3/2006 | Gan et al. |
| 7,022,506 B2 | 4/2006 | Brighton et al. |
| 7,089,060 B1 | 8/2006 | Fitzsimmons |
| 7,130,692 B2 | 10/2006 | Brighton et al. |
| 7,160,241 B1 | 1/2007 | Herbst |
| 7,175,587 B2 | 2/2007 | Gordon et al. |
| 7,177,695 B2 | 2/2007 | Moran |
| 7,177,696 B1 | 2/2007 | Pandelisev |
| 7,215,995 B2 | 5/2007 | Brighton et al. |
| 7,288,062 B2 | 10/2007 | Spiegel |
| 7,333,858 B2 | 2/2008 | Killian et al. |
| 7,429,471 B2 | 9/2008 | Brighton |
| 7,456,189 B2 | 11/2008 | Himmelsbach et al. |
| 7,465,546 B2 | 12/2008 | Brighton |
| 7,465,566 B2 | 12/2008 | Brighton et al. |
| 7,520,849 B1 | 4/2009 | Simon |
| 7,566,295 B2 | 7/2009 | Giardino et al. |
| 7,740,574 B2 | 6/2010 | Pilla et al. |
| 7,744,524 B2 | 6/2010 | Pilla |
| 7,758,490 B2 | 7/2010 | Pilla et al. |
| 7,896,797 B2 | 3/2011 | Pilla et al. |
| 2001/0007937 A1 | 7/2001 | MacKin |
| 2001/0031906 A1 | 10/2001 | Ishikawa et al. |
| 2001/0044643 A1 | 11/2001 | Litovitz |
| 2002/0035358 A1 | 3/2002 | Wang |
| 2003/0023283 A1 | 1/2003 | McDaniel |
| 2003/0028072 A1 | 2/2003 | Fischell et al. |
| 2003/0093028 A1 | 5/2003 | Spiegel |
| 2003/0099979 A1 | 5/2003 | Ohtani et al. |
| 2003/0125769 A1 | 7/2003 | Brighton |
| 2003/0171640 A1 | 9/2003 | Canedo |
| 2004/0176803 A1 | 9/2004 | Whelan et al. |
| 2004/0176805 A1 | 9/2004 | Whelan et al. |
| 2004/0176806 A1 | 9/2004 | Markoll |
| 2004/0267333 A1 | 12/2004 | Kronberg |
| 2005/0049640 A1 | 3/2005 | Gurtner et al. |
| 2005/0059153 A1 | 3/2005 | George et al. |
| 2005/0215842 A1 | 9/2005 | Pilla et al. |
| 2005/0222625 A1 | 10/2005 | Laniado et al. |
| 2005/0251229 A1 | 11/2005 | Pilla et al. |
| 2006/0009825 A1 | 1/2006 | Chiriaev et al. |
| 2006/0161226 A1 | 7/2006 | McMickle |
| 2006/0206174 A1 | 9/2006 | Honeycutt et al. |
| 2006/0212077 A1 | 9/2006 | Pilla et al. |
| 2007/0026514 A1 | 2/2007 | Pilla et al. |
| 2007/0173904 A1 | 7/2007 | Pilla |
| 2007/0282156 A1 | 12/2007 | Konings |
| 2007/0299472 A1 | 12/2007 | Brighton |
| 2008/0058793 A1 | 3/2008 | Pilla et al. |
| 2008/0132971 A1 | 6/2008 | Pille et al. |
| 2008/0140155 A1 | 6/2008 | Pilla et al. |
| 2009/0030476 A1 | 1/2009 | Hargrove |
| 2010/0210893 A1 | 8/2010 | Pilla |
| 2010/0222631 A1 | 9/2010 | Pilla |
| 2011/0112352 A1 | 5/2011 | Pilla et al. |
| 2011/0152598 A1 | 6/2011 | Pilla et al. |
| 2011/0207989 A1 | 8/2011 | Pilla et al. |

FOREIGN PATENT DOCUMENTS

| | | |
|---|---|---|
| DE | 970276 | 9/1958 |
| EP | 543152 A2 | 10/1992 |
| EP | 0500983 | 7/1995 |
| FR | 748828 | 4/1933 |
| GB | 0604107 | 6/1948 |
| GB | 2162066 | 1/1986 |
| GB | 2400316 A | 10/2004 |
| JP | 03-523271 | 8/2003 |
| WO | WO 83/01742 A1 | 5/1983 |
| WO | WO 95/27533 | 10/1995 |
| WO | WO 96/11723 | 4/1996 |
| WO | WO 2004/108208 A2 | 12/2004 |

OTHER PUBLICATIONS

Anderson et al.; Fluoro-jade B stains quiescent and reactive astrocytes in the rodent spinal cord. J Neurotrauma 20, 1223-31 (Nov. 2003).

Arnold et al.; Nitric oxide activates guanylate cyclase and increases guanosine 3':5'-cyclic monophosphate levels in various tissue preparations. Proc Natl Acad Sci U S A 74, 3203-7 (Aug. 1977).

Bassett et al.; Generation of electric potentials by bone in response to mechanical stress. Science 137, 1063-4 (Sep. 28, 1962).

Bassett, C. A.; Biological significance of piezoelectricity. Calc. Tiss. Res. 1, 252 (Dec. 1968).

Beaumont et al.; The effects of human corticotrophin releasing factor on motor and cognitive deficits after impact acceleration injury. Neurol Res 22, 665-73 (Oct. 2000).

Beaumont et al.; The impact-acceleration model of head injury: injury severity predicts motor and cognitive performance after trauma. Neurol Res 21, 742-54 (Dec. 1999).

Beck et al.; The Bioelectromagnetics Society (History of the first 25 years); eds. Shappard, A. and Blackman, C.; 46 pgs.; (mo. unavailable) 2004.

Becker, T. O.; The bioelectric factors in amphibian limb regeneration. J. Bone Joint Surg. 43A, 643 (Jul. 1961).

Bederson et al.; Nuclear magnetic resonance imaging and spectroscopy in experimental brain edema in a rat model. J Neurosurg 64, 795-802 (May 1986).

Blackman et al.; Action of 50 Hz magnetic fields on neurite outgrowth in pheochromocytoma cells. Bioelectromagnetics 14, 273-86 (mo. unavailable) (1993).

Borbely et al.; Pulsed high-frequency electromagnetic field affects human sleep and sleep electroencephalogram. Neurosci Lett 275, 207-10 (Nov. 19, 1999).

Bracken et al.; Administration of methylprednisolone for 24 or 48 hours or tirilazad mesylate for 48 hours in the treatment of acute spinal cord injury. Results of the Third National Acute Spinal Cord Injury Randomized Controlled Trial. National Acute Spinal Cord Injury Study. Jama 277, 1597-604 (May 28, 1997).

Bredt, D. S.; Nitric oxide signaling specificity—the heart of the problem. J Cell Sci 116, 9-15 (Jan. 2003).

Brighton et al.; Signal transduction in electrically stimulated bone cells. J Bone Joint Surg Am 83-A, 1514-23 (Oct. 2001).

Brighton, C. T.; The treatment of non-unions with electricity. J Bone Joint Surg Am 63, 847-51 (Jun. 1981).

Brooks et al.; Magnetic resonance spectroscopy in traumatic brain injury. J Head Trauma Rehabil 16, 149-64 (Apr. 2001).

Cammermeyer, J.; I. An evaluation of the significance of the "dark" neuron. Ergeb Anat Entwicklungsgesch 36, 1-61 (mo. unavailable) (1962).

Canals et al.; Neurotrophic and neurotoxic effects of nitric oxide on fetal midbrain cultures. J Neurochem 76, 56-68 (Jan. 2001).

Casper et al.; Dopaminergic neurons associate with blood vessels in neural transplants. Exp Neurol 184, 785-93 (Dec. 2003).

Casper et al.; Enhanced vascularization and survival of neural transplants with ex vivo angiogenic gene transfer. Cell Transpl. 11, 331-349 (mo. unavailable) (2002).

Cernak et al.; Cognitive deficits following blast injury-induced neurotrauma: possible involvement of nitric oxide. Brain Inj 15, 593-612 (Jul. 2001).

Cernak et al.; Ultrastructural and functional characteristics of blast injury-induced neurotrauma. J Trauma 50, 695-706 (Apr. 2001).

Ciani et al.; Akt pathway mediates a cGMP-dependent survival role of nitric oxide in cerebellar granule neurones. J Neurochem 81, 218-28 (Apr. 2002).

Cook et al.; Resting EEG is affected by exposure to a pulsed ELF magnetic field. Bioelectromagnetics 25, 196-203 (Apr. 2004).

Cook et al.; The effects of pulsed, high-frequency radio waves on the rate of osteogenesis in the healing of extraction wounds in dogs; Oral Sug.; 32(6); (Dec. 1971).

Cork et al.; Computer-aided analysis of polarized neurite growth. Effects of applied electrical fields on neuronal development. J Neurosci Methods 32, 45-54 (Apr. 1990).

Csuka et al.; IL-10 levels in cerebrospinal fluid and serum of patients with severe traumatic brain injury: relationship to IL-6, TNF-alpha, TGF-beta1 and blood-brain barrier function. J Neuroimmunol 101, 211-21 (Nov. 1999).

De Olmos et al.; Use of an amino-cupric-silver technique for the detection of early and semiacute neuronal degeneration caused by neurotoxicants, hypoxia, and physical trauma. Neurotoxicol Teratol 16, 545-61 (Nov. 1994).

Dixon et al.; A controlled cortical impact model of traumatic brain injury in the rat. J Neurosci Methods 39, 253-62 (Oct. 1991).

Dixon et al.; A fluid percussion model of experimental brain injury in the rat. J Neurosurg 67, 110-9 (Jul. 1987).

Fabre et al.; Antidepressant efficacy and cognitive effects of repetitive transcranial magnetic stimulation in vascular depression: an open trial. Int J Geriatr Psychiatry 19, 833-42 (Sep. 2004).

Farndale et al.; The action of pulsed magnetic fields on cyclic AMP levels in cultured fibroblasts. Biochim Biophys Acta 881, 46-53 (Mar. 19, 1986).

Fassbender et al.; Temporal profile of release of interleukin-1beta in neurotrauma. Neurosci Lett 284, 135-8 (Apr. 2000).

Foda et al.; A new model of diffuse brain injury in rats. Part II: Morphological characterization. J Neurosurg 80, 301-13 (Feb. 1994).

Foley-Nolan et al.; Pulsed high frequency (27MHz) electromagnetic therapy for persistent neck pain. A double blind, placebo-controlled study of 20 patients. Orthopedics 13, 445-51 (Apr. 1990).

Friedman et al.; Quantitative proton MRS predicts outcome after traumatic brain injury. Neurology 52, 1384-91 (Apr. 1999).

Fukada et al.; On the piezoelectric effect of bone. J Phys Soc Japan 12 (10), 1158-1162 (Oct. 1957).

Gaetz, M.; The neurophysiology of brain injury. Clin Neurophysiol 115, 4-18 (Jan. 2004).

Garthwaite et al.; Cyclic GMP and cell death in rat cerebellar slices. Neuroscience 26, 321-6 (Jul. 1988).

Gasparovic et al.; Decrease and recovery of N-acetylaspartate/creatine in rat brain remote from focal injury. J Neurotrauma 18, 241-6 (Mar. 2001).

Ghirnikar et al.; Inflammation in traumatic brain injury: role of cytokines and chemokines. Neurochem Res 23, 329-40 (Mar. 1998).

Gona et al.; Effects of 60 Hz electric and magnetic fields on the development of the rat cerebellum. Bioelectromagnetics 14, 433-47 (mo. unavailable) (1993).

Goodwin et al.; A double-blind study of capacitively coupled electrical stimulation as an adjunct to lumbar spinal fusions(printed from online source). Spine 24(13), 1349-1357 (Jul. 1999).

Graeber et al.; New expression of myelomonocytic antigens by microglia and perivascular cells following lethal motor neuron injury. J Neuroimmunol 27, 121-32 (May 1990).

Greenebaum et al.; Effects of pulsed magnetic fields on neurite outgrowth from chick embryo dorsal root ganglia. Bioelectromagnetics 17, 293-302 (mo. unavailable) (1996).

Ignarro et al.; Heme-dependent activation of guanylate cyclase by nitric oxide: a novel signal transduction mechanism. Blood Vessels 28, 67-73 (Nov.-Dec. 1991).

Ito et al.; Characterization of edema by diffusion-weighted imaging in experimental traumatic brain injury. J Neurosurg 84, 97-103 (Jan. 1996).

Jackson et al.; The demonstration of new human brain-specific proteins by high-resolution two-dimensional polyacrylamide gel electrophoresis. J Neurol Sci 49, 429-38; (Mar. 1981).

Jenrow et al.; Weak ELF magnetic field effects on hippocampal rhythmic slow activity. Exp Neurol 153, 328-34 (Oct. 1998).

Jokela et al.; Assessment of the magnetic field exposure due to the battery current of digital mobile phones. Health Phys 86, 56-66 (Jan. 2004).

Kanje et al.; Pretreatment of rats with pulsed electromagnetic fields enhances regeneration of the sciatic nerve. Bioelectromagnetics 14, 353-9 (mo. unavailable) (1993).

Kingham et al.; Microglial secreted cathepsin B induces neuronal apoptosis. J Neurochem 76, 1475-84 (Mar. 2001).

Knowles et al.; Nitric oxide synthases in mammals. Biochem J 298, 249-58 (Mar. 1994).

Kossmann et al.; Intrathecal and serum interleukin-6 and the acute-phase response in patients with severe traumatic brain injuries. Shock 4, 311-7 (Nov. 1995).

Kramarenko et al.; Effects of high-frequency electromagnetic fields on human EEG: a brain mapping study. Int J Neurosci 113, 1007-19 (Jul. 2003).

Lai et al.; Magnetic-field-induced DNA strand breaks in brain cells of the rat. Environ Health Perspect 112, 687-94 (May 2004).

LeDoux, J.; Emotion: clues from the brain. Annu Rev Psychol 46, 209-35 (Jan. 1995).

Lee et al.; Nitric oxide in the healing wound: a time-course study. J Surg Res 101, 104-8 (Nov. 2001).

Lee et al.; Pulsed magnetic and electromagnetic fields in experimental achilles tendonitis in the rat: a prospective randomized study. Arch Phys Med Rehabil 78, 399-404 (Apr. 1997).

Lighthall, J. W.; Controlled cortical impact: a new experimental brain injury model. J Neurotrauma 5, 1-15 (mo. unavailable) (1988).

Lincoln et al.; Low frequency of pathogenic mutations in the ubiquitin carboxy-terminal hydrolase gene in familial Parkinson's disease. Neuroreport 10, 427-9 (Feb. 1999).

Linovitz et al.; Combined magnetic fields accelerate and increase spine fusion: a double-blind, randomized, placebo controlled study(printed from online source). Spine 27, 1383-1389 (Jul. 2002).

Maas et al.; Why have recent trials of neuroprotective agents in head injury failed to how convincing efficacy? A pragmatic analysis and theoretical considerations. (printed from online source) Neurosurgery 44, 1286-98 (Jun. 1999).

Maeda et al.; Effect of water on piezoelectric, dielectric, and elastic properties of bone; Biopolymers 21(10); 2055-2068 (Oct. 1982).

Marmarou et al.; A new model of diffuse brain injury in rats. Part I: Pathophysiology and biomechanics. J Neurosurg 80, 291-300 (Feb. 1994).

McFarlane et al.; Changes in neurite outgrowth but not in cell division induced by low EMF exposure: influence of field strength and culture conditions on responses in rat PC12 pheochromocytoma cells. Bioelectrochemistry 52, 23-8 (Sep. 2000).
McIntosh et al.; Traumatic brain injury in the rat: characterization of a lateral fluid-percussion model. Neuroscience 28(1), 233-44 (mo. unavailable) (1989).
McIntosh et al.; Traumatic brain injury in the rat: characterization of a midline fluid-percussion model. Cent Nerv Syst Trauma 4, 119-34 (mo. unavailable) (1987).
Mellor, S.; The pathogenesis of blast injury and its management. Br J Hosp Med 39, 536-9 (Jun. 1988).
Morganti-Kossmann et al.; Production of cytokines following brain injury: beneficial and deleterious for the damaged tissue. Mol Psychiatry 2, 133-6 (Mar. 1997).
Morris et al.; Place navigation impaired in rats with hippocampal lesions. Nature 297, 681-3 (Jun. 1982).
Naldini et al.; Role of inflammatory mediators in angiogenesis. Curr Drug Targets Inflamm Allergy 4, 3-8 (Feb. 2005).
Narayan et al.; Clinical trials in head injury (Author Manuscript). J Neurotrauma 19, 503-57 (May 2002).
Nauta et al.; Silver impregnation of degenerating axons in the central nervous system: a modified technic. Stain Technol 29, 91-3 (Mar. 1954).
Northington et al.; Early Neurodegeneration after Hypoxia-Ischemia in Neonatal Rat Is Necrosis while Delayed Neuronal Death Is Apoptosis. Neurobiol Dis 8, 207-19 (Apr. 2001).
Oda et al.; Magnetic field exposure saves rat cerebellar granule neurons from apoptosis in vitro. Neurosci Lett 365, 83-6 (Jul. 22, 2004).
Pantazis et al.; The nitric oxide-cyclic GMP pathway plays an essential role in both promoting cell survival of cerebellar granule cells in culture and protecting the cells against ethanol neurotoxicity. J Neurochem 70, 1826-38 (May 1998).
Patino et al.; Pulsed electromagnetic fields in experimental cutaneous wound healing in rats. J Burn Care Rehabil 17, 528-31 (Nov./Dec. 1996).
Paylor et al.; Inbred strain differences in prepulse inhibition of the mouse startle response. Psychopharmacology (Berl) 132, 169-80 (Jul. 1997).
Pennington et al.; Pulsed, non-thermal, high-frequency electromagnetic energy (Diapulse) in the treatment of grade I and grade II ankle sprains. Mil Med 158, 101-4 (Feb. 1993).
Pilla et al.; Gap junction impedance tissue dielectrics and thermal noise limits for electromagnetic field bioeffects; Bioelectrochemistry and Bioenergetics; vol. 35; pp. 63-69; Nov. 1994.
Pilla; State of the art in electromagnetic therapeutics: soft tissue applications; Electricity and Magnetism in Biology and Medicine; Bersani (ed.); Kluwer Academic/Plenum Publishers; pp. 871-874; (month unavailable) 1999.
Pirozzoli et al.; Effects of 50 Hz electromagnetic field exposure on apoptosis and differentiation in a neuroblastoma cell line. Bioelectromagnetics 24, 510-6 (Oct. 2003).
Rogers et al.; Behavioral and functional analysis of mouse phenotype: SHIRPA, a proposed protocol for comprehensive phenotype assessment. Mamm Genome 8, 711-3 (Oct. 1997).
Saljo et al.; Exposure to short-lasting impulse noise causes microglial and astroglial cell activation in the adult rat brain. Pathophysiology 8, 105-111 (Dec. 2001).
Salzberg et al.; The effects of non-thermal pulsed electromagnetic energy on wound healing of pressure ulcers in spinal cord-injured patients: a randomized, double-blind study. Ostomy Wound Manage 41, 42-4, 46, 48 passim (Apr. 1995).
Sandyk, R.; Treatment with AC pulsed electromagnetic fields improves olfactory function in Parkinson's disease. Int J Neurosci 97, 225-33 (Apr. 1999).
Sapolsky; Glucocorticoid toxicity in the hippocampus: temporal aspects of neuronal vulnerability. Brain Res 359, 300-5 (Dec. 16, 1985).
Sauerland et al.; Risks and benefits of preoperative high dose methylprednisolone in surgical patients: a systematic review. Drug Saf 23, 449-61 (Nov. 2000).
Schmued et al.; Fluoro-Jade: a novel fluorochrome for the sensitive and reliable histochemical localization of neuronal degeneration. Brain Res 751, 37-46 (Mar. 1997).
Seegers et al.; Activation of signal-transduction mechanisms may underlie the therapeutic effects of an applied electric field. Med Hypotheses 57, 224-30 (Aug. 2001).
Shupak et al.; Human exposure to a specific pulsed magnetic field: effects on thermal sensory and pain thresholds. Neurosci Lett 363, 157-62 (Jun. 10, 2004).
Slepko et al.; Progressive activation of adult microglial cells in vitro. Glia 16, 241-46 (Mar. 1996).
Stahel et al.; The role of the complement system in traumatic brain injury. Brain Res Brain Res Rev 27, 243-56 (Jul. 1998).
Steinberg et al.; Results of core decompression and grafting with and without electrical stimulation. Clin Orthop, 199-208 (Dec. 1989).
Tehranian et al.; Improved recovery and delayed cytokine induction after closed head injury in mice with central overexpression of the secreted isoform of the interleukin-1 receptor antagonist. J Neurotrauma 19, 939-51 (Aug. 2002).
Thurman et al.; The epidemiology of sports-related traumatic brain injuries in the United States: recent developments. J Head Trauma Rehabil 13, 1-8 (Apr. 1998).
Unterberg et al.; Edema and brain trauma. Neuroscience 129(4), 1021-9 (mo. unavailable) (2004).
Weissman et al.; Activation and inactivation of neuronal nitric oxide synthase: characterization of $Ca(2+)$-dependent [125I]Calmodulin binding. Eur J Pharmacol 435, 9-18 (Jan. 2002).
Wenk, G.; The nucleus basalis magnocellularis cholinergic system: one hundred years of progress; Neurobiology of Learning and Memory; 67(2); 85-95 (Mar. 1997).
Williams et al.; Characterization of a new rat model of penetrating ballistic brain injury. J Neurotrauma 22, 313-31 (Feb. 2005).
Yasuda, I.; Part III. Clinical Studies: Mechanical and electrical callus; Annals of the New York Academy of Sciences; vol. 238; pp. 457-465 (Oct. 1974).
Yu et al.; Effects of 60 Hz electric and magnetic fields on maturation of the rat neopallium. Bioelectromagnetics 14, 449-58 (mo. unavailable) (1993).
Zizic et al.; The treatment of osteoarthritis of the knee with pulsed electrical stimulation. J Rheumatol 22, 1757-61 (Sep. 1995).
DiMino et al.; U.S. Appl. No. 13/361,797 entitled "Method and devices for providing electromagnetic treatment in the presence of a metal-containing implant," filed Jan. 30, 2012.
Aaron et al.; Power frequency fields promote cell differentiation coincident with an increase in transforming growth factor-?1 expression; bioelectromagnetics; vol. 20; pp. 453-458; 1999.
Aaron et al.; The conservative treatment of osteonecrosis of the femoral head. A comparison of core decompression and pulsing electromagnetic fields; Clin. Orthopaed. Rel. Res.; vol. 249; pp. 209-218; 1989.
Adair; A physical analysis of the ion parametric resonance model; Bioelectromagnetics; vol. 19; pp. 181-191; 1998.
Adair; Criticism of Lednev's mechanism for the influence of weak magnetic fields on biological systems; Bioelectromagnetics; vol. 13; pp. 231-235; 1992.
Adair; Static and low-frequency magnetic field effects: Health risks and therapies; Rep Prog Phys; vol. 63; pp. 415-454; 2000.
Akai et al.; Effect of electrical stimulation on musculoskeletal systems: a meta-analysis of controlled clinical trials; Bioelectromagnetics; vol. 23; pp. 132-143; 2002.
Ayrapetyan et al.; Magnetic fields alter electrical properties of solutions and their physiological effects; Bioelectromagnetics; vol. 15; pp. 133-142; 1994.
Bassett et al.; A non-operative salvage of surgically-resistant pseudoarthroses and non-unions by pulsing electromagnetic fileds; Clin Orthop; vol. 124; pp. 117-131; 1977.
Bawin et al.; Effects of modulated VHF fields on the central nervous system; ANN NYAcad Sci; vol. 247; pp. 74-81; 1975.
Bawin et al.; Sensitivity of calcium binding in cerebral tissue to weak environmental electric fields oscillating at low frequency; Proc Natl Acad Sci, USA; pp. 1999-2003; 1976.
Bearden Jr.; Quantitation of submicrogram quantities of protein by an improved protein-dye binding assay; Biochim Biophys Acta; vol. 533; pp. 525-529; 1978.

Belyaev et al.; Frequency-dependent Effects of ELF Magnetic Field on Cromatin Conformation in *Escherichia coli* Cells and Human Lymphocytes; Biochimica et Biophysica Acta; vol. 1526; pp. 269-276; 2001.

Binder et al.; Pulsed electromagnetic field therapy of persistent rotator cuff tendinitis: a double blind controlled assessment; Lancet; vol. 1 (8379); pp. 695-697; 1984.

Blackman et al.; A role for the magnetic field in the radiation induced efflux of calcium ions from brain tissue in vitro; Bioelectromagnetics; vol. 6; pp. 327-337; 1985.

Blackman et al.; Empirical test of an ion parametric resonance model for magnetic field interactions with PC-12 cells; Bioelectromagnetics; vol. 15: pp. 239-260; 1994.

Blackman et al.; Influence of electromagnetic fields on the efflux of calcium ions from brain tissue in vitro: A three-model analysis consistent with the frequency response up to 510 Hz; Bioelectromagnetics; vol. 9; pp. 215-227; 1988.

Blackman et al.; Multiple power-density windows and their possible origin; Bioelectromagnetics; vol. 10; pp. 115-128; 1989.

Blanchard et al.; Clarification and application of an ion parametric resonance model for magnetic field interactions with biological systems; Bioelectromagnetics; vol. 15; pp. 217-238; 1994.

Blank et al.; Do electromagnetic fields interact directly with DNA?; Bioelectromagnetics; vol. 18; pp. 111-115; 1997.

Blumenthal et al.; Effects of low-intensity AC and/or DC electromagnetic fields on cell attachment and induction of apoptosis; Bioelectromagnetics; vol. 18; pp. 264-272; 1997.

Cain; Stimulating Treatment; Orthopedic Technology Review; vol. 4; No. 4; pp. 31-34; 2002.

Chiabrera et al.; Effect of Lifetimes on Ligand Binding Modelled by the Density Operator; Bioelectrochemistry and Bioenergetics; vol. 30; pp. 35-42; 1993.

Clapham, D.; Calcium signaling; Cell; vol. 80; pp. 259-268; 1995.

Colbert et al.; Magnetic mattress pad use in patients with fibromyalgia: A randomized double-blind pilot study; J Back Musculoskeletal Rehab; vol. 13; 19-31; 1999.

Collacott et al.; Bipolar permanent magnets for the treatment of low back pain: A pilot study; JAMA; vol. 283; No. 10; pp. 1322-1325; Mar. 8, 2000.

Cox, J.; Interactive Properties of Calmodulin; Biochem J.; vol. 249; pp. 621-629; 1988.

Edmonds, D.; Larmor precession as a mechanism for the detection of static and alternating magnetic fields; Bioelectrochemistry and Bioenergetics; vol. 30; pp. 3-12; 1993.

Engström, S.; Dynamic properties of Lednev's parametric resonance mechanism; Bioelectromagnetics; vol. 17; pp. 58-70; 1996.

Fitzsimmons et al.; Combined magnetic fields increase net calcium flux in bone cells. Calcif. Tiss. Intl.; vol. 55; pp. 376-380; 1994.

Halle, B.; On the cyclotron resonance mechanism for magnetic field effects on transmembrane ion conductivity; Bioelectromagnetics; vol. 9; pp. 381-385; 1988.

Johansson, et al.; Brij 58, a polyoxethylene acyl ether, creates membrane vesicles of uniform sidedness: A new tool to obtain inside-out (cytoplasmic side-out) plasma membrane vesicle; Plant J.; vol. 7; pp. 165-173; 1995.

Kloth et al.; Effect of Pulsed Radio Frequency Stimulation on Wound Healing: A Double-Blind Pilot Clinical Study; in "Electricity and Magnetism in Biology and Medicine"; Bersani F, ed Plenum, New York; pp. 875-878; 1999.

Koch, et al.; Interaction between weak low-frequency magnetic fields and cell membranes; Bioelectromagnetics; vol. 24; pp. 39-402; 2003.

Körner et al.; Surface properties of right side-out plasma membrane vesicles isolated from barley roots and leaves; Plant Physiol.; vol. 79; pp. 72-79; 1985.

Lansdown et al.; Sequential changes in trace metal, metallothionein and calmodulin concentrations in healing skin wounds; J. Anat.; vol. 195; pp. 375-386; 1999.

Larsson et al.; Isolation of highly purified plant plasma membranes and separation of inside-out and rightside-out vesicles; Methods Enzymol; vol. 228; pp. 451-469; 1994.

Liboff, et al.; Geomagnetic cyclotron resonance in living cells; J Biol Phys; vol. 9; pp. 99-102; 1985.

Liboff, et al.; Kinetics of channelized membrane ions in magnetic fields; Bioelectromagnetics; vol. 9; pp. 39-51; 1988.

Likic et al.; Dynamics of Ca2+-saturated Calmodulin D129N Mutant Studied by Multiple Molecular Dynamics Simulations; Protein Sci; vol. 12; pp. 2215-2229; 2003.

Lukas, T.; A Signal Transduction Pathway Model Prototype II: Application to Ca21-Calmodulin Signaling and Myosin Light Chain Phosphorylatiori; Biophysical Journal; vol. 87; pp. 1417-1425; 2004.

Man, et al.; The influence of permanent magnetic field therapy on wound healing in suction lipectomy patients: A double-blind study; Plastic and Reconstructive Surgery; vol. 104; pp. 2261-2296; 1999 (printed Jul. 17, 2010).

Markov, et al.; Weak static magnetic field modulation of myosin phosphorylation in a cell-free preparation: Calcium dependence; Bioelectrochemistry and Bioenergetics; vol. 43; pp. 233,238; 1997.

McDonald, F.; Effect of static magnetic fields on osteoblasts and fibroblasts in-vitro; Bioelectomagnetics; vol. 14; pp. 187-196; 1993.

McLean, et al.; Blockade of sensory neuron action potentials by a static magnetic field in the 10 mT range; Bioelectromagnetics; vol. 16; pp. 20-32; 1995.

McLeod, et al.; Dynamic characteristics of membrane ions in multifield configurations of low-frequency electromagnetic radiation; Bioelectromagnetics; vol. 7; pp. 177-189; 1986.

Mehler, et al.; Structural Dynamics of Calmodulin and Troponin C; Protein Engineering; vol. 4; No. 6; pp. 625-627; 1991.

Mooney; A randomized double blind prospective study of the efficacy of pulsed electromagnetic fields for interbody lumbar fusions; Spine; vol. 15; pp. 708-715; 1990.

Muehsam et al.; Lorentz Approach to Static Magnetic Field Effects on Bound Ion Dynamics and Binding Kinetics: Thermal Noise Considerations; Bioelectromagnetics; vol. 17; pp. 89-99; 1996.

Muehsam et al.; Weak Magnetic Field Modulation of Ion Dynamics in a Potential Well: Mechanistic and Thermal Noise Considerations; Bioelectrochem Bioenergetics; vol. 28; pp. 355-365; 1994.

Muehsam, et al.; The sensitivity of cells and tissues to exogenous fields: effects of target system initial state; Bioelectrochemistry and Bioenergetics; vol. 48; pp. 35-42; 1999.

Pilla et al.; EMF signals and ion/ligand binding kinetics:prediction of bioeffective waveform parameters; Bioelectrochemistry and Bioenergetics; vol. 48; pp. 27-34; 1999.

Pilla; Electrochemical information transfer at living cell membrane; Ann. N.Y.Acad. Sci.; vol. 238; p. 149-170; 1974.

Pilla; Low-intensity electromagnetic and mechanical modulation of bone growth and repair: are they equivalent?; Journal of Orthopedic Science; vol. 7; pp. 420-428; 2002.

Pilla; Weak time-varying and static magnetic fields: from Mechanisms to therapeutic applications; Biological Effects of Electro Magnetic Fields; P. Stavroulakis, ed. Springer Veriag; pp. 34-75; 2003.

Ryaby et al.; The role of insulin-like growth factor in magnetic field regulation of bone formation. Bioelectrochem. Bioenergetics; vol. 35; pp. 87-91; 1994.

Valbona, et al.; Response of pain to static magnetic fields in postpolio patients: A doubleblind pilot study; Arch Phys. Med. Rehabil.; vol. 78; pp. 1200-1203; 1997.

Weaver, et al.; The response of living cells to very weak electric fields: The thermal noise limit; Science; vol. 247; pp. 459-462; 1990.

Zhadin, M.; Combined action of static and alternating magnetic fields on ion motion in a macromolecule; Theoretical aspects; Bioelectromagnetics; vol. 19; pp. 279-292; 1998.

Zhuang et al.; Electrical stimulation induces the level of TGF-B 1 mRNA in osteoblastic cells by amechanism involving calcium/calmodulin pathway; Biochem. Biophys. Res. Comm.; vol. 237;pp. 225-229; 1997.

Zdeblick; A prospective, randomized study of lumbar fusion: preliminary results; Spine; vol. 18; pp. 983-991; 1993.

Pilla et al.; U.S. Appl. No. 13/252,114 entitled "Method and apparatus for electromagnetic treatment of head, cerebral and neural injury in animals and humans," filed Oct. 2, 2011.

Pilla, Arthur A.; U.S. Appl. No. 13/285,761 entitled "Method and apparatus for electromagnetic enhancement of biochemical signaling pathways for therapeutics and prophylaxis in plants, animals and humans," filed Oct. 31, 2011.

Blackman et al.; Effects of ELF fields on calcium-ion efflux from brain tissue in vitro; Radiat Res; vol. 92(3); pp. 510-520; Dec. 1982.

Chiabrera et al.; Bioelectromagnetic Resonance Interactions: Endogenous Field and Noise. In "Interaction Mechanisms of Low-Level Electromagnetic Fields in Living Systems." Oxford University Press. 164.179; Dec. 1992.

Chiabrera et al.; Quantum dynamics of ions in molecular crevices under electromagnetic exposure; (Brighton C, Pollak S, editors); Electromagnetics in biology and medicine; San Francisco, USA; San Francisco Press; pp. 21-26; Jun. 1991.

Chiabrera et al.; The role of the magnetic field in the EM interaction with ligand binding; In: "Mechanistic Approaches to Interaction of Electric and Electromagnetic Fields With Living Systems;" Blank, Findl (eds); New York; Plenum Press; pp. 79-95; Oct. 31, 1987.

Ginsberg, A. J.; Ultrashort radio waves as a therapeutic agent. Med Record 140, 651-653 (Dec. 19, 1934).

Goligorsky et al.; Relationships between caveolae and eNOS: everything in proximity and the proximity of everything; Am J Physiol Renal Physiol; 283; pp. F1-F10; Jul. 2002.

Hart, F.; A quantum mechanical model for bioelectromagnetic resonance phenomena; J Bioelectr; vol. 9; pp. 1-7; Jan. 1990.

Itoh et al.; Accelerated wound healing of pressure ulcers by pulsed high peak power electromagnetic energy (Diapulse). Decubitus 4(1), pp. 24-5, 29-30, 32 & 34 (Feb. 1991).

Jones et al.; Low energy time varying electromagnetic field interactions with cellular control mechanisms; In: fMechanistic approaches to interactions of electric and electromagnetic fields with living systemsf; Blank, Findl (eds); Plenum Press; NY; pp. 389-397; Oct. 31, 1987.

Kimura et al.; Reciprocol regulation between nitric oxide and vascular endothelial growth factor in angiogenesis; Acta Biochimica Polonica; vol. 50, No. 1; pp. 49-59; (year of publication is sufficiently earlier than the effective U.S. filed and any foreign priority date) 2003.

Kjellbom et al.; Preparation and polypeptide composition of chlorophyll-free plasma membranes from leaves of light-grown spinach and barley; Physiol Plant; vol. 62; pp. 501-509; Dec. 1984.

Lednev, V.; Possible mechanism for the effect of weak magnetic fields on biological systems: Correction of the basic expression and its consequences; In: Electricity and magnetism in biology and medicine Blank (eds.); San Francisco, CA; San Francisco Press, Inc.; pp. 550-552; Oct. 1993.

Lednev, V.; Possible mechanism for the influence of weak magnetic fields on biological systems; Bioelectromagnetics; vol. 12; pp. 71-75; (year of publication is sufficiently earlier than the effective U.S. filing date and any foreign priority date) 1991.

Liboff, et al.; Experimental evidence for ion cyclotron resonance mediation of membrane transport; In: Blank, Findl (eds.); Mechanical approaches to interactions of electric and electromagnetic fields with living systems; Blank, Findl (eds.); New York; Plenum Press; pp. 281-296; Oct. 31, 1987.

Ohkubo et al.; Acute effects of static magnetic fields on cutaneous microcirculation in rabbits; in Vivo; vol. 11; pp. 221-226; May-Jun. 1997.

Okano et al.; Biphasic effects of static magnetic fields on cutaneous microcirculation in rabbits; Bioelectromagnetics; vol. 20(3); pp. 161-171; (year of publication is sufficiently earlier than the effective U.S. filing and any foreign priority date) 1999.

Olbe et al.; The spinach plasma membrane $Ca2^+$ pump is a 120-kDa polypeptide regulated by calmodulinbinding to a terminal region; Physiol Plantarum; vol. 103; pp. 35-44; May 1998.

Pilla; Electrochemical information and energy transfer in vivo; Proc. 7th IECEC;Washington, D.C.; American Chemical Society; pp. 761-64; (year of publication is sufficiently earlier than the effective U.S. filing date and any foreign priority date) 1972.

Pineros et al.; Calcium channels in higher plant cells: Selectivity, regulation, and pharmacology; J Exp. Bot; vol. 48; special issue; pp. 551-577; Mar. 1997.

Ramundo-Orlando, et al.; Effect of Low Frequency, Low Amplitude Magnetic Fields on the Permeability of Cationic Liposomes Entrapping Carbonic Anhydrase I. Evidence for Charged Lipid Involvement; Bioelectromagnetics; vol. 21; pp. 491-498; Oct. 2000.

Sagan, L.; Epidemiological and laboratory studies of power frequency electric and magnetic fields; JAMA; vol. 268(5); pp. 625-629; Aug. 5, 1992.

Sarimov, et al.; Exposure to ELF Magnetic Field Tuned to Zn Inhibits Growth of Cancer Cells. Bioelectromagnetics; vol. 26; No. 8; pp. 631-638; Dec. 2005.

Sisken et al.; Prospects on clinical applications of electrical stimulation for nerve regeneration. J Cell Biochem 52, 404-409 (Apr. 1993).

Smith, S.; Calcium cyclotron resonance and diatom mobility; Bioelectromagnetics; vol. 8; pp. 215-227; (year of publication is sufficiently earlier than the effective U.S. filing date and any foreign priority date) 1987.

Teleman et al.; Kinetics of Ca2+ binding to calmodulin and its tryptic fragments studied by 43Ca-NMR. Biochim Biophys Acta 873, 204-13 (Sep. 1986).

Trillo et al.; Magnetic fields at resonant conditions for the hydrogen ion affect neurite outgrowth in PC-12 cells: a test of the ion parametric resonance model. Bioelectromagnetics 17, 10-20 (year of publication is sufficiently earlier than the effective U.S. filing date any foreign priority date) (1996).

Weinstein, et al.; Ca2+-Binding and Structural Dynamics in the functions of Calmodulin; Ann. Rev. Physiol; vol. 56; pp. 213-236; Mar. 1994.

Weintraub, M.; Magnetic bio-stimulation in painful diabetic peripheral neuropathy: a novel intervention R a randomized double-placebo crossover study; Am J Pain Manag; vol. 9; pp. 8-17; Jan. 1, 1999.

Yumoto, et al.; Coordination Structures of Ca2+ and Mg2+ in Akazara Scallop Troponin C in Solution; Eur. J. Biochem; vol. 268(23); pp. 6284-6290; Dec. 2001.

Zhadin, et al.; Frequency and Amplitude Windows in the Combined Action of DC and Low Frequency AC Magnetic Fields on Ion Thermal Motion in a Macromolecule: Theoretical Analysis; Bioelectromagnetics; vol. 26; issue 4; pp. 323-330; May 2005.

Zhadin, et al.; Ion Cyclotron Resonance in Biomolecules; Biomed Sci; vol. 1; pp. 245-250; (year of publication is sufficiently earlier than the effective U.S. filing date and any foreign priority date) 1990.

ELECTROMAGNETIC TREATMENT APPARATUS AND METHOD FOR ANGIOGENESIS MODULATION OF LIVING TISSUES AND CELLS

This application is a Divisional application of U.S. Non-Provisional application Ser. No. 11/110,000 filed Apr. 19, 2005 hereby incorporated by reference and claims the benefit of U.S. Provisional Application 60/563,104 filed Apr. 19, 2004 hereby incorporated by reference.

BACKGROUND OF THE INVENTION

1. Field of the Invention

This invention pertains generally to an apparatus and a method for treatment of living tissues and cells by altering their interaction with their electromagnetic environment. This invention also relates to a method of modification of cellular and tissue growth, repair, maintenance, and general behavior by application of encoded electromagnetic information. More particularly this invention relates to the application of surgically non-invasive coupling of highly specific electromagnetic signal patterns to any number of body parts. In particular, an embodiment according to the present invention pertains to using pulsing electromagnetic fields ("PEMF") to enhance living tissue growth and repair via angiogenesis and neovascularization by affecting the precursors to growth factors and other cytokines, such as ion/ligand binding such as calcium binding to calmodoulin.

2. Discussion of Related Art

It is now well established that application of weak non-thermal electromagnetic fields ("EMF") can result in physiologically meaningful in vivo and in vitro bioeffects.

EMF has been used in applications of bone repair and bone healing. Waveforms comprising low frequency components and low power are currently used in orthopedic clinics. Origins of using bone repair signals began by considering that an electrical pathway may constitute a means through which bone can adaptively respond to EMF signals. A linear physicochemical approach employing an electrochemical model of a cell membrane predicted a range of EMF waveform patterns for which bioeffects might be expected. Since a cell membrane was a likely EMF target, it became necessary to find a range of waveform parameters for which an induced electric field could couple electrochemically at the cellular surface, such as voltage-dependent kinetics. Extension of this linear model also involved Lorentz force analysis.

A pulsed radio frequency ("PRF") signal derived from a 27.12 MHz continuous sine wave used for deep tissue healing is known in the prior art of diathermy. A pulsed successor of the diathermy signal was originally reported as an electromagnetic field capable of eliciting a non-thermal biological effect in the treatment of infections. PRF therapeutic applications have been reported for reduction of post-traumatic and post-operative pain and edema in soft tissues, wound healing, burn treatment and nerve regeneration. Application of EMF for the resolution of traumatic edema has become increasingly used in recent years. Results to date using PRF in animal and clinical studies suggest that edema may be measurably reduced from such electromagnetic stimulus.

Prior art considerations of EMF dosimetry have not taken into account dielectric properties of tissue structure as opposed to the properties of isolated cells.

In recent years, clinical use of non-invasive PRF at radio frequencies comprised using pulsed bursts of a 27.12 MHz sinusoidal wave, wherein each pulse burst comprises a width of sixty-five microseconds, having approximately 1,700 sinusoidal cycles per burst, and various burst repetition rates. By use of a substantially single voltage amplitude envelope with each PRF burst, one was limiting frequency components that could couple to relevant dielectric pathways in cells and tissue.

Time-varying electromagnetic fields, comprising rectangular waveforms such as pulsing electromagnetic fields, and sinusoidal waveforms such as pulsed radio frequency fields ranging from several Hertz to an about 15 to an about 40 MHz range, are clinically beneficial when used as an adjunctive therapy for a variety of musculoskeletal injuries and conditions.

Beginning in the 1960's, development of modern therapeutic and prophylactic devices was stimulated by clinical problems associated with non-union and delayed union bone fractures. Early work showed that an electrical pathway can be a means through which bone adaptively responds to mechanical input. Early therapeutic devices used implanted and semi-invasive electrodes delivering direct current ("DC") to a fracture site. Non-invasive technologies were subsequently developed using electrical and electromagnetic fields. These modalities were originally created to provide a non-invasive "no-touch" means of inducing an electrical/mechanical waveform at a cell/tissue level. Clinical applications of these technologies in orthopaedics have led to approved applications by regulatory bodies worldwide for treatment of fractures such as non-unions and fresh fractures, as well as spine fusion. Presently several EMF devices constitute the standard armamentarium of orthopaedic clinical practice for treatment of difficult to heal fractures. The success rate for these devices has been very high. The database for this indication is large enough to enable its recommended use as a safe, non-surgical, non-invasive alternative to a first bone graft. Additional clinical indications for these technologies have been reported in double blind studies for treatment of avascular necrosis, tendinitis, osteoarthritis, wound repair, blood circulation and pain from arthritis as well as other musculoskeletal injuries.

Cellular studies have addressed effects of weak low frequency electromagnetic fields on both signal transduction pathways and growth factor synthesis. It can be shown that EMF stimulates secretion of growth factors after a short, trigger-like duration. Ion/ligand binding processes at a cell membrane are generally considered an initial EMF target pathway structure. The clinical relevance to treatments for example of bone repair, is upregulation such as modulation, of growth factor production as part of normal molecular regulation of bone repair. Cellular level studies have shown effects on calcium ion transport, cell proliferation, Insulin Growth Factor ("IGF-II") release, and IGF-II receptor expression in osteoblasts. Effects on Insulin Growth Factor-I ("IGF-I") and IGF-II have also been demonstrated in rat fracture callus. Stimulation of transforming growth factor beta ("TGF-β") messenger RNA ("mRNA") with PEMF in a bone induction model in a rat has been shown. Studies have also demonstrated upregulation of TGF-β mRNA by PEMF in human osteoblast-like cell line designated MG-63, wherein there were increases in TGF-β1, collagen, and osteocalcin synthesis. PEMF stimulated an increase in TGF-β1 in both hypertrophic and atrophic cells from human non-union tissue. Further studies demonstrated an increase in both TGF-β1 mRNA and protein in osteoblast cultures resulting from a direct effect of EMF on a calcium/calmodulin-dependent pathway. Cartilage cell studies have shown similar increases in TGF-β1 mRNA and protein synthesis from EMF, demonstrating a therapeutic application to joint repair. Various studies conclude that upregulation of growth factor production may be a common denominator in the tissue level mechanisms underlying electromagnetic stimulation. When using specific inhibitors, EMF can act through a calmodulin-dependent pathway. It has been previously reported that specific PEMF and PRF signals, as well as weak static magnetic fields, modulate $Ca^{2+}$ binding to CaM in a cell-free enzyme preparation. Additionally, upregulation of mRNA for BMP2 and BMP4 with PEMF in osteoblast cultures and upregulation of TGF-β1 in bone and cartilage with PEMF have been demonstrated.

However, prior art in this field does not configure waveforms based upon a ion/ligand binding transduction pathway. Prior art waveforms are inefficient since prior art waveforms apply unnecessarily high amplitude and power to living tissues and cells, require unnecessarily long treatment time, and cannot be generated by a portable device.

Therefore, a need exists for an apparatus and a method that more effectively modulates angiogenesis and other biochemical processes that regulate tissue growth and repair, shortens treatment times, and incorporates miniaturized circuitry and light weight applicators thus allowing the apparatus to be portable and if desired disposable. A further need exists for an apparatus and method that more effectively modulates angiogenesis and other biochemical processes that regulate tissue growth and repair, shortens treatment times, and incorporates miniaturized circuitry and light weight applicators that can be constructed to be implantable.

SUMMARY OF THE INVENTION

An apparatus and a method for electromagnetic treatment of living tissues and cells by altering their interaction with their electromagnetic environment.

According to an embodiment of the present invention, by treating a selectable body region with a flux path comprising a succession of EMF pulses having a minimum width characteristic of at least about 0.01 microseconds in a pulse burst envelope having between about 1 and about 100,000 pulses per burst, in which a voltage amplitude envelope of said pulse burst is defined by a randomly varying parameter in which instantaneous minimum amplitude thereof is not smaller than the maximum amplitude thereof by a factor of one ten-thousandth. The pulse burst repetition rate can vary from about 0.01 to about 10,000 Hz. A mathematically definable parameter can also be employed to define an amplitude envelope of said pulse bursts.

By increasing a range of frequency components transmitted to relevant cellular pathways, access to a large range of biophysical phenomena applicable to known healing mechanisms, including enhanced enzyme activity and growth factor and cytokine release, is advantageously achieved.

According to an embodiment of the present invention, by applying a random, or other high spectral density envelope, to a pulse burst envelope of mono- or bi-polar rectangular or sinusoidal pulses which induce peak electric fields between $10^{-6}$ and 10 volts per centimeter (V/cm), a more efficient and greater effect can be achieved on biological healing processes applicable to both soft and hard tissues in humans, animals and plants. A pulse burst envelope of higher spectral density can advantageously and efficiently couple to physiologically relevant dielectric pathways, such as, cellular membrane receptors, ion binding to cellular enzymes, and general transmembrane potential changes thereby modulating angiogenesis and neovascularization.

By advantageously applying a high spectral density voltage envelope as a modulating or pulse-burst defining parameter, power requirements for such modulated pulse bursts can be significantly lower than that of an unmodulated pulse. This is due to more efficient matching of the frequency components to the relevant cellular/molecular process. Accordingly, the dual advantages of enhanced transmitting dosimetry to relevant dielectric pathways and of decreasing power requirements are achieved.

A preferred embodiment according to the present invention utilizes a Power Signal to Noise Ratio ("Power SNR") approach to configure bioeffective waveforms and incorporates miniaturized circuitry and lightweight flexible coils. This advantageously allows a device that utilizes a Power SNR approach, miniaturized circuitry, and lightweight flexible coils, to be completely portable and if desired to be constructed as disposable and if further desired to be constructed as implantable.

Specifically, broad spectral density bursts of electromagnetic waveforms, configured to achieve maximum signal power within a bandpass of a biological target, are selectively applied to target pathway structures such as living organs, tissues, cells and molecules. Waveforms are selected using a unique amplitude/power comparison with that of thermal noise in a target pathway structure. Signals comprise bursts of at least one of sinusoidal, rectangular, chaotic and random wave shapes, have frequency content in a range of about 0.01 Hz to about 100 MHz at about 1 to about 100,000 bursts per second, and have a burst repetition rate from about 0.01 to about 1000 bursts/second. Peak signal amplitude at a target pathway structure such as tissue, lies in a range of about 1 µV/cm to about 100 mV/cm. Each signal burst envelope may be a random function providing a means to accommodate different electromagnetic characteristics of healing tissue. A preferred embodiment according to the present invention comprises about 0.1 to about 100 millisecond pulse burst comprising about 1 to about 200 microsecond symmetrical or asymmetrical pulses repeating at about 0.1 to about 100 kilohertz within the burst. The burst envelope is a modified 1/f function and is applied at random repetition rates between about 0.1 and about 1000 Hz. Fixed repetition rates can also be used between about 0.1 Hz and about 1000 Hz. An induced electric field from about 0.001 mV/cm to about 100 mV/cm is generated. Another embodiment according to the present invention comprises an about 0.01 millisecond to an about 10 millisecond burst of high frequency sinusoidal waves, such as 27.12 MHz, repeating at about 1 to about 100 bursts per second. An induced electric field from about 0.001 mV/cm to about 100 mV/cm is generated. Resulting waveforms can be delivered via inductive or capacitive coupling.

It is an object of the present invention to provide modulation of electromagnetically sensitive regulatory processes at the cell membrane and at junctional interfaces between cells.

It is another object of the present invention to provide an electromagnetic method of treatment of living cells and tissues comprising a broad-band, high spectral density electromagnetic field.

It is a further object of the present invention to provide an electromagnetic method of treatment of living cells and tissues comprising amplitude modulation of a pulse burst envelope of an electromagnetic signal that will induce coupling with a maximum number of relevant EMF-sensitive pathways in cells or tissues.

It is another object of the present invention to provide increased blood flow to affected tissues by modulating angiogenesis and neovascualrization.

It is another object of the present invention to provide increased blood flow to enhance viability, growth, and differentiation of implanted cells, such as stem cells, tissues and organs.

It is another object of the present invention to provide increased blood flow in cardiovascular diseases by modulating angiogenesis and neovascualarization.

It is another object of the present invention to improve micro-vascular blood perfusion and reduced transudation.

It is another object of the present invention to provide a treatment of maladies of the bone and other hard tissue by modulating angiogenesis and neovascularization.

It is a still further object of the present invention to provide a treatment of edema and swelling of soft tissue by increased blood flow through modulation of angiogenesis and neovascularization.

It is another object of the present invention to provide an electromagnetic method of treatment of living cells and tissues that can be used for repair of damaged soft tissue.

It is yet another object of the present invention to increase blood flow to damaged tissue by modulation of vasodilation and stimulating neovascularization.

It is a yet further object of the present invention to provide an apparatus for modulation of angiogenesis and neovascularization that can be operated at reduced power levels and still possess benefits of safety, economics, portability, and reduced electromagnetic interference.

It is an object of the present invention to configure a power spectrum of a waveform by mathematical simulation by using signal to noise ratio ("SNR") analysis to configure a waveform optimized to modulate angiogensis and neovascualarization then coupling the configured waveform using a generating device such as ultra lightweight wire coils that are powered by a waveform configuration device such as miniaturized electronic circuitry.

It is another object of the present invention to modulate angiogenesis and neovascularization by evaluating Power SNR for any target pathway structure such as molecules, cells, tissues and organs of plants, animals and humans using any input waveform, even if electrical equivalents are non-linear as in a Hodgkin-Huxley membrane model.

It is another object of the present invention to provide a method and apparatus for treating plants, animals and humans using electromagnetic fields selected by optimizing a power spectrum of a waveform to be applied to a biochemical target pathway structure to enable modulation of angiogenesis and neovascularization within molecules, cells, tissues and organs of a plant, animal, and human.

It is another object of the present invention to significantly lower peak amplitudes and shorter pulse duration. This can be accomplished by matching via Power SNR, a frequency range in a signal to frequency response and sensitivity of a target pathway structure such as a molecule, cell, tissue, and organ, of plants, animals and humans to enable modulation of angiogenesis and neovascularization.

The above and yet other objects and advantages of the present invention will become apparent from the hereinafter set forth Brief Description of the Drawings, Detailed Description of the Invention, and Claims appended herewith.

BRIEF DESCRIPTION OF THE DRAWINGS

Preferred embodiments of the present invention will be described below in more detail, with reference to the accompanying drawings.

DETAILED DESCRIPTION

Figure 1:
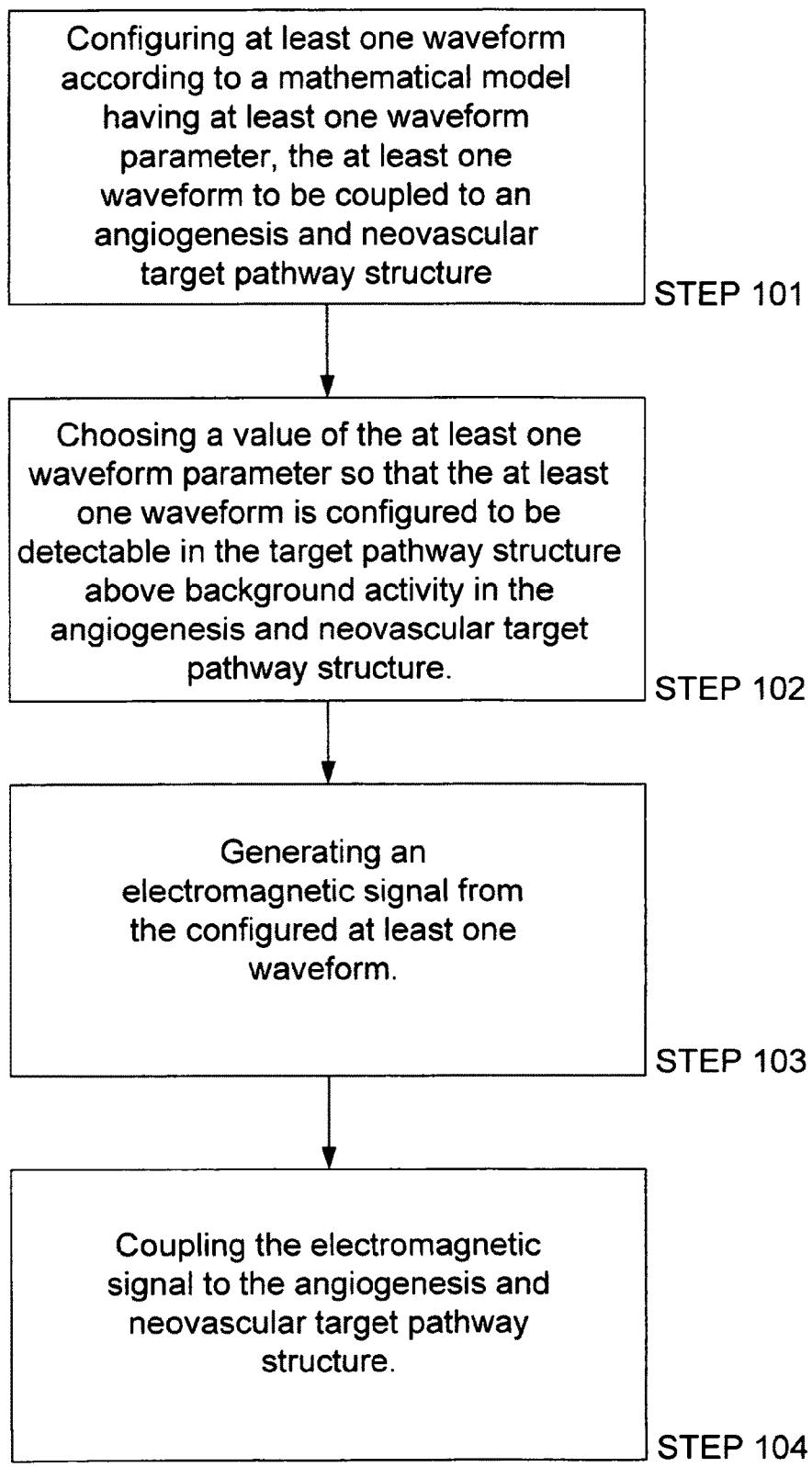
FIG. 1 is a flow diagram of a electromagnetic treatment method for angiogenesis modulation of living tissues and cells according to an embodiment of the present invention.

Induced time-varying currents from PEMF or PRF devices flow in a target pathway structure such as a molecule, cell, tissue, and organ, and it is these currents that are a stimulus to which cells and tissues can react in a physiologically meaningful manner. The electrical properties of a target pathway structure affect levels and distributions of induced current. Molecules, cells, tissue, and organs are all in an induced current pathway such as cells in a gap junction contact. Ion or ligand interactions at binding sites on macromolecules that may reside on a membrane surface are voltage dependent processes, that is electrochemical, that can respond to an induced electromagnetic field ("E"). Induced current arrives at these sites via a surrounding ionic medium. The presence of cells in a current pathway causes an induced current ("J") to decay more rapidly with time ("J(t)"). This is due to an added electrical impedance of cells from membrane capacitance and time constants of binding and other voltage sensitive membrane processes such as membrane transport.

Equivalent electrical circuit models representing various membrane and charged interface configurations have been derived. For example, in Calcium ("$Ca^{2+}$") binding, the change in concentration of bound $Ca^{2+}$ at a binding site due to induced E may be described in a frequency domain by an impedance expression such as:

$$Z_b(\omega) = R_{ion} + \frac{1}{i\omega C_{ion}}$$

which has the form of a series resistance-capacitance electrical equivalent circuit. Where $\omega$ is angular frequency defined as $2\pi f$, where f is frequency, $i=-1\frac{1}{2}$, $Z_b(\omega)$ is the binding impedance, and $R_{ion}$ and $C_{ion}$ are equivalent binding resistance and capacitance of an ion binding pathway. The value of the equivalent binding time constant, $\tau_{ion}=R_{ion}C_{ion}$, is related to a ion binding rate constant, $k_b$, via $\tau_{ion}=R_{ion}C_{ion}=1/k_b$. Thus, the characteristic time constant of this pathway is determined by ion binding kinetics.

Induced E from a PEMF or PRF signal can cause current to flow into an ion binding pathway and affect the number of $Ca^{2+}$ ions bound per unit time. An electrical equivalent of this is a change in voltage across the equivalent binding capacitance $C_{ion}$, which is a direct measure of the change in electrical charge stored by $C_{ion}$. Electrical charge is directly proportional to a surface concentration of $Ca^{2+}$ ions in the binding site, that is storage of charge is equivalent to storage of ions or other charged species on cell surfaces and junctions. Electrical impedance measurements, as well as direct kinetic analyses of binding rate constants, provide values for time constants necessary for configuration of a PMF waveform to match a bandpass of target pathway structures. This allows for a required range of frequencies for any given induced E waveform for optimal coupling to target impedance, such as bandpass.

Ion binding to regulatory molecules is a frequent EMF target, for example $Ca^{2+}$ binding to calmodulin ("CaM"). Use of this pathway is based upon acceleration of wound repair, for example bone repair, that involves modulation of growth factors released in various stages of repair. Growth factors such as platelet derived growth factor ("PDGF"), fibroblast growth factor ("FGF"), and epidermal growth factor ("EGF") are all involved at an appropriate stage of healing. Angiogenesis and neovascularization are also integral to wound repair and can be modulated by PMF. All of these factors are Ca/CaM-dependent.

Utilizing a Ca/CaM pathway a waveform can be configured for which induced power is sufficiently above background thermal noise power. Under correct physiological conditions, this waveform can have a physiologically significant bioeffect.

Application of a Power SNR model to Ca/CaM requires knowledge of electrical equivalents of $Ca^{2+}$ binding kinetics at CaM. Within first order binding kinetics, changes in concentration of bound $Ca^{2+}$ at CaM binding sites over time may be characterized in a frequency domain by an equivalent binding time constant, $\tau_{ion}=R_{ion}C_{ion}$, where $R_{ion}$ and $C_{ion}$ are equivalent binding resistance and capacitance of the ion binding pathway. $\tau_{ion}$ is related to a ion binding rate constant, $k_b$, via $\tau_{ion}=R_{ion}C_{ion}=1/k_b$. Published values for $k_b$ can then be employed in a cell array model to evaluate SNR by comparing voltage induced by a PRF signal to thermal fluctuations in voltage at a CaM binding site. Employing numerical values for PMF response, such as $V_{max}=6.5\times10^{-7}$ sec$^{-1}$, $[Ca^{2+}]=2.5$ μM, $K_D=30$ μM, $[Ca^{2+}CaM]=K_D([Ca^{2+}]+[CaM])$, yields $k_b=665$ sec$^{-1}$ ($\tau_{ion}=1.5$ msec). Such a value for $\tau_{ion}$ can be employed in an electrical equivalent circuit for ion binding while power SNR analysis can be performed for any waveform structure.

According to an embodiment of the present invention a mathematical model can be configured to assimilate that thermal noise is present in all voltage dependent processes and represents a minimum threshold requirement to establish adequate SNR. Power spectral density, $S_n(\omega)$, of thermal noise can be expressed as:

$$S_n(\omega)=4kT\,Re[Z_M(x,\omega)]$$

where $Z_M(x,\omega)$ is electrical impedance of a target pathway structure, x is a dimension of a target pathway structure and Re denotes a real part of impedance of a target pathway structure. $Z_M(x,\omega)$ can be expressed as:

$$Z_M(x,\omega) = \left[\frac{R_e + R_i + R_g}{\gamma}\right]\tanh(\gamma x)$$

This equation clearly shows that electrical impedance of the target pathway structure, and contributions from extracellular fluid resistance ("$R_e$"), intracellular fluid resistance ("$R_i$") and intermembrane resistance ("$R_g$") which are electrically connected to a target pathway structure, all contribute to noise filtering.

A typical approach to evaluation of SNR uses a single value of a root mean square (RMS) noise voltage. This is calculated by taking a square root of an integration of $S_n(\omega)=4kT\,Re[Z_M(x,\omega)]$ over all frequencies relevant to either complete membrane response, or to bandwidth of a target pathway structure. SNR can be expressed by a ratio:

$$SNR = \frac{|V_M(\omega)|}{RMS}$$

where $|V_M(\omega)|$ is maximum amplitude of voltage at each frequency as delivered by a chosen waveform to the target pathway structure.

An embodiment according to the present invention comprises a pulse burst envelope having a high spectral density, so that the effect of therapy upon the relevant dielectric pathways, such as, cellular membrane receptors, ion binding to cellular enzymes and general transmembrane potential changes, is enhanced. Accordingly by increasing a number of frequency components transmitted to relevant cellular pathways, a large range of biophysical phenomena, such as modulating growth factor and cytokine release and ion binding at regulatory molecules, applicable to known healing mechanisms is accessible. According to an embodiment of the present invention applying a random, or other high spectral density envelope, to a pulse burst envelope of mono- or bipolar rectangular or sinusoidal pulses inducing peak electric fields between about $10^{-6}$ and about 100 V/cm, produces a greater effect on biological healing processes applicable to both soft and hard tissues.

According to yet another embodiment of the present invention by applying a high spectral density voltage envelope as a modulating or pulse-burst defining parameter, power requirements for such amplitude modulated pulse bursts can be significantly lower than that of an unmodulated pulse burst containing pulses within a similar frequency range. This is due to a substantial reduction in duty cycle within repetitive burst trains brought about by imposition of an irregular, and preferably random, amplitude onto what would otherwise be a substantially uniform pulse burst envelope. Accordingly, the dual advantages, of enhanced transmitted dosimetry to the relevant dielectric pathways and of decreased power requirement are achieved.

Referring to FIG. 1, wherein FIG. 1 is a flow diagram of a method for delivering electromagnetic signals to angiogenesis and neovascularization target pathway structures such as ions and ligands of plants, animals, and humans for therapeutic and prophylactic purposes according to an embodiment of the present invention. A mathematical model having at least one waveform parameter is applied to configure at least one waveform to be coupled to a angiogenesis and neovascularization target pathway structure such as ions and ligands (Step 101). The configured waveform satisfies a SNR or Power SNR model so that for a given and known angiogenesis and neovascularization target pathway structure it is possible to choose at least one waveform parameter so that a waveform is detectable in the angiogenesis and neovascularization target pathway structure above its background activity (Step 102) such as baseline thermal fluctuations in voltage and electrical impedance at a target pathway structure that depend upon a state of a cell and tissue, that is whether the state is at least one of resting, growing, replacing, and responding to injury. A preferred embodiment of a generated electromagnetic signal is comprised of a burst of arbitrary waveforms having at least one waveform parameter that includes a plurality of frequency components ranging from about 0.01 Hz to about 100 MHz wherein the plurality of frequency components satisfies a Power SNR model (Step 102). A repetitive electromagnetic signal can be generated for example inductively or capacitively, from said configured at least one waveform (Step 103). The electromagnetic signal is coupled to a angiogenesis and neovascularization target pathway structure such as ions and ligands by output of a coupling device such as an electrode or an inductor, placed in close proximity to the target pathway structure (Step 104). The coupling enhances modulation of binding of ions and ligands to regulatory molecule in living tissues and cells.

Figure 2:
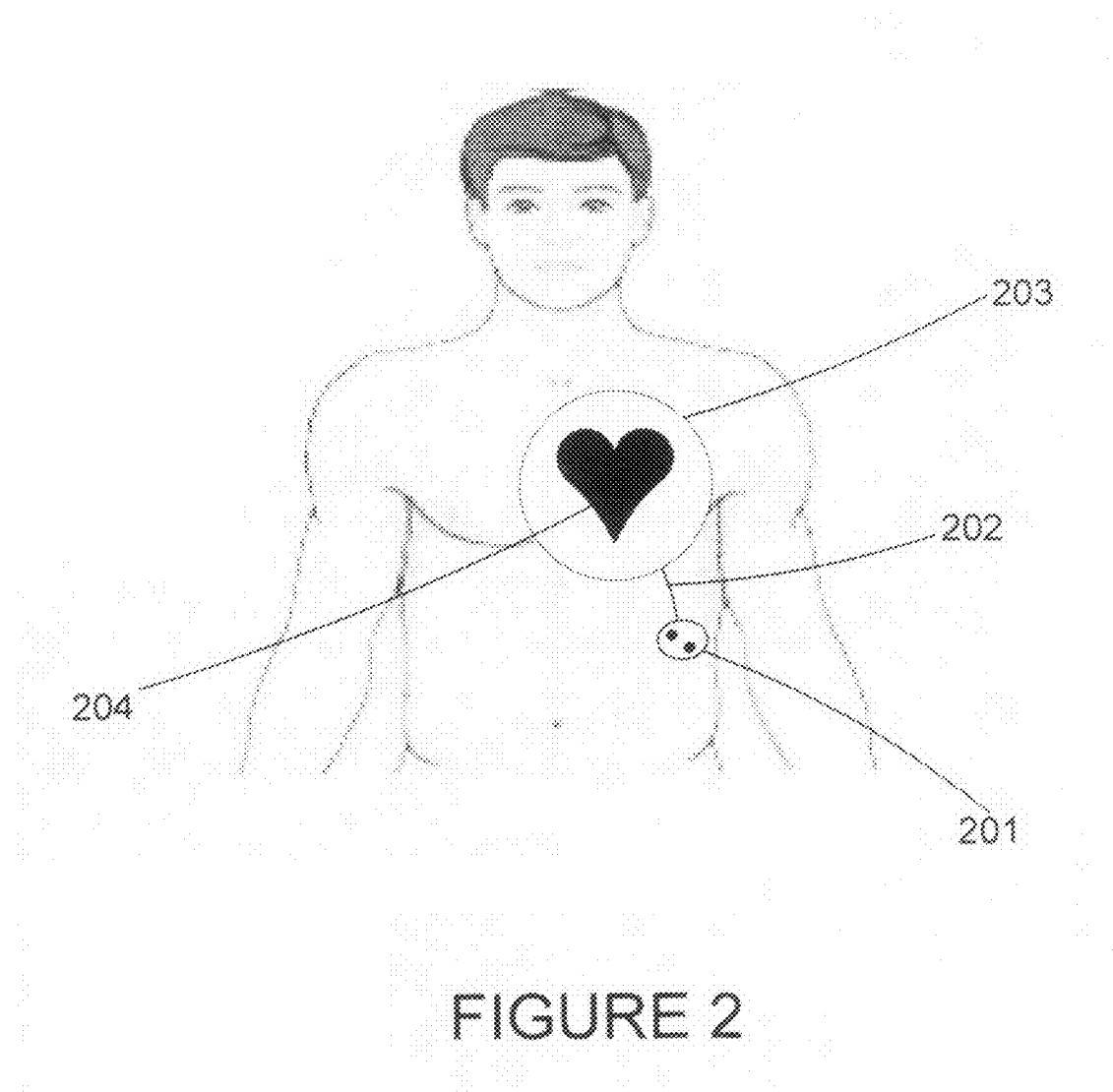
FIG. 2 is a view of control circuitry according to a preferred embodiment of the present invention.

FIG. 2 illustrates a preferred embodiment of an apparatus according to the present invention. A miniature control circuit 201 is coupled to an end of at least one connector 202 such as wire. The opposite end of the at least one connector is coupled to a generating device such as a pair of electrical coils 203. The miniature control circuit 201 is constructed in a manner that applies a mathematical model that is used to configure waveforms. The configured waveforms have to satisfy a SNR or Power SNR model so that for a given and known angiogenesis and neovascularization target pathway structure, it is possible to choose waveform parameters that satisfy SNR or Power SNR so that a waveform is detectable in the angiogenesis and neovascularization target pathway structure above its background activity. A preferred embodiment according to the present invention applies a mathematical model to induce a time-varying magnetic field and a time-varying electric field in a angiogenesis and neovascularization target pathway structure such as ions and ligands, comprising about 10 to about 100 msec bursts of about 1 to about 100 microsecond rectangular pulses repeating at about 0.1 to about 10 pulses per second. Peak amplitude of the induced electric field is between about 1 uV/cm and about 100 mV/cm, varied according to a modified 1/f function where f=frequency. A waveform configured using a preferred embodiment according to the present invention may be applied to a angiogenesis and neovascularization target pathway structure such as ions and ligands for a preferred total exposure time of under 1 minute to 240 minutes daily. However other exposure times can be used. Waveforms configured by the miniature control circuit 201 are directed to a generating device 203 such as electrical coils via connector 202. The generating device 203 delivers a pulsing magnetic field configured according to a mathematical model, that can be used to provide treatment to a angiogenesis and neovascularization target pathway structure such as a heart in a chest 204. The miniature control circuit applies a pulsing magnetic field for a prescribed time and can automatically repeat applying the pulsing magnetic field for as many applications as are needed in a given time period, for example 10 times a day. A preferred embodiment according to the present invention can be positioned to treat the heart in a chest 204 by a positioning device. Coupling a pulsing magnetic field to a angiogenesis and neovascularization target pathway structure such as ions and ligands, therapeutically and prophylactically reduces inflammation thereby reducing pain and promotes healing. When electrical coils are used as the generating device 203, the electrical coils can be powered with a time varying magnetic field that induces a time varying electric field in a target pathway structure according to Faraday's law. An electromagnetic signal generated by the generating device 203 can also be applied using electrochemical coupling, wherein electrodes are in direct contact with skin or another outer electrically conductive boundary of a target pathway structure. Yet in another embodiment according to the present invention, the electromagnetic signal generated by the generating device 203 can also be applied using electrostatic coupling wherein an air gap exists between a generating device 203 such as an electrode and a angiogenesis and neovascularization target pathway structure such as ions and ligands. An advantage of the preferred embodiment according to the present invention is that its ultra lightweight coils and miniaturized circuitry allow for use with common physical therapy treatment modalities and at any body location for which pain relief and healing is desired. An advantageous result of application of the preferred embodiment according to the present invention is that a living organism's angiogenesis and neovascularization can be maintained and enhanced.

Figure 3:
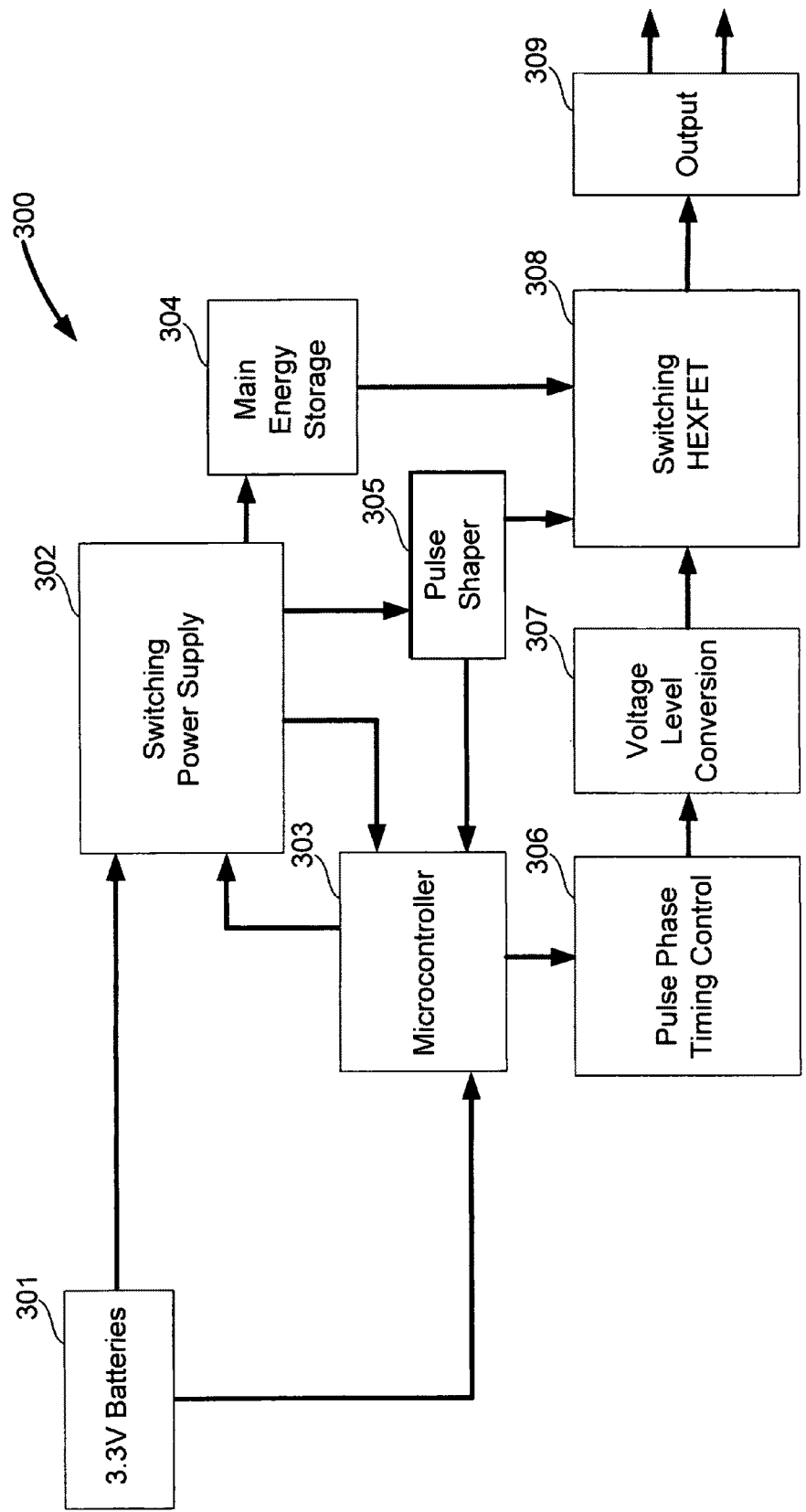
FIG. 3 is a block diagram of miniaturized circuitry according to a preferred embodiment of the present invention.

FIG. 3 depicts a block diagram of a preferred embodiment according to the present invention of a miniature control circuit 300. The miniature control circuit 300 produces waveforms that drive a generating device such as wire coils described above in FIG. 2. The miniature control circuit can be activated by any activation means such as an on/off switch. The miniature control circuit 300 has a power source such as a lithium battery 301. A preferred embodiment of the power source has an output voltage of 3.3 V but other voltages can be used. In another embodiment according to the present invention the power source can be an external power source such as an electric current outlet such as an AC/DC outlet, coupled to the present invention for example by a plug and wire. A switching power supply 302 controls voltage to a micro-controller 303. A preferred embodiment of the micro-controller 303 uses an 8 bit 4 MHz micro-controller 303 but other bit MHz combination micro-controllers may be used. The switching power supply 302 also delivers current to storage capacitors 304. A preferred embodiment of the present invention uses storage capacitors having a 220 uF output but other outputs can be used. The storage capacitors 304 allow high frequency pulses to be delivered to a coupling device such as inductors (Not Shown). The micro-controller 303 also controls a pulse shaper 305 and a pulse phase timing control 306. The pulse shaper 305 and pulse phase timing control 306 determine pulse shape, burst width, burst envelope shape, and burst repetition rate. An integral waveform generator, such as a sine wave or arbitrary number generator can also be incorporated to provide specific waveforms. A voltage level conversion sub-circuit 308 controls an induced field delivered to a target pathway structure. A switching Hexfet 308 allows pulses of randomized amplitude to be delivered to output 309 that routes a waveform to at least one coupling device such as an inductor. The micro-controller 303 can also control total exposure time of a single treatment of a target pathway structure such as a molecule, cell, tissue, and organ. The miniature control circuit 300 can be constructed to apply a pulsing magnetic field for a prescribed time and to automatically repeat applying the pulsing magnetic field for as many applications as are needed in a given time period, for example 10 times a day. A preferred embodiment according to the present invention uses treatments times of about 10 minutes to about 30 minutes.

Figure 4:
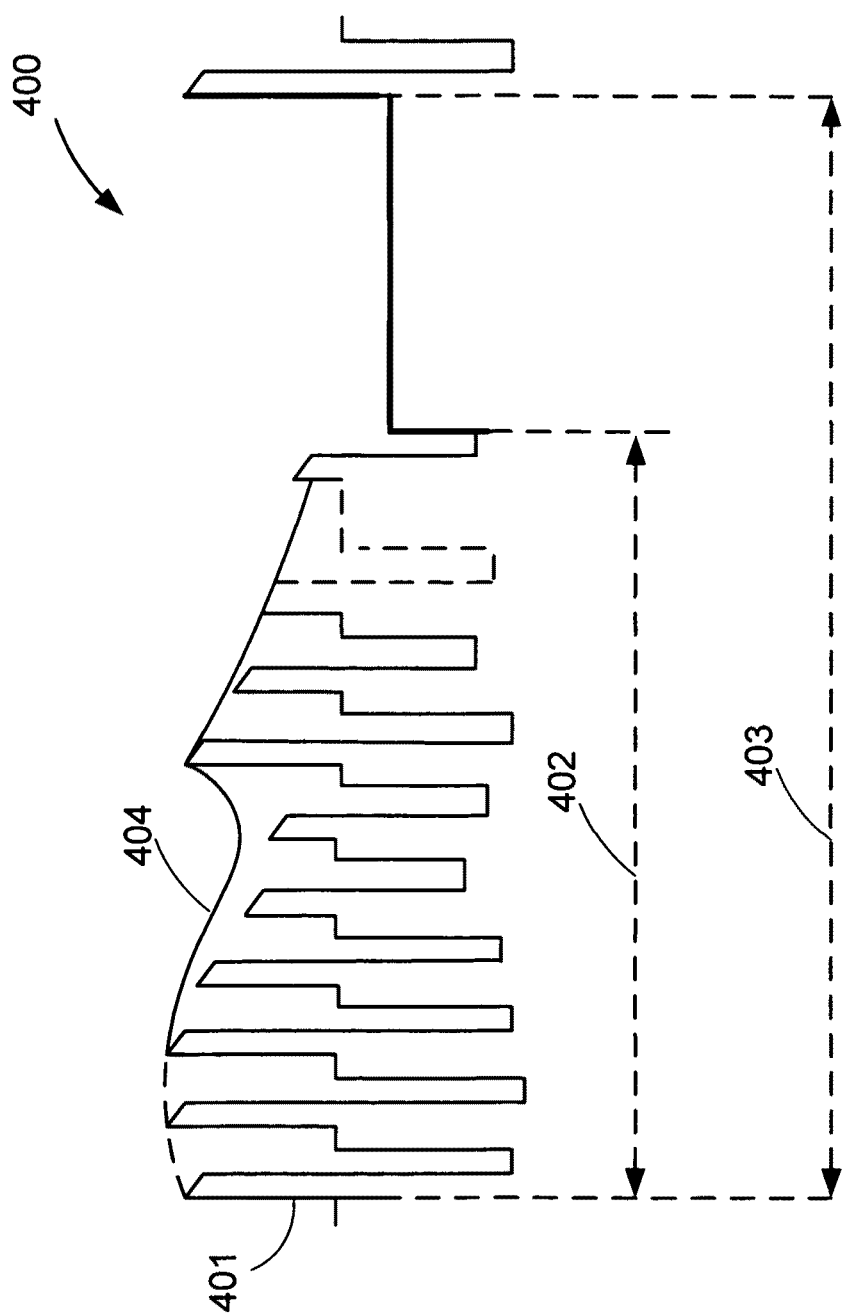
FIG. 4 depicts a waveform delivered to a angiogenesis and neovascularization target pathway structure according to a preferred embodiment of the present invention.

Referring to FIG. 4 an embodiment according to the present invention of a waveform 400 is illustrated. A pulse 401 is repeated within a burst 402 that has a finite duration 403. The duration 403 is such that a duty cycle which can be defined as a ratio of burst duration to signal period is between about 1 to about $10^{-5}$. A preferred embodiment according to the present invention utilizes pseudo rectangular 10 microsecond pulses for pulse 401 applied in a burst 402 for about 10 to about 50 msec having a modified 1/f amplitude envelope 404 and with a finite duration 403 corresponding to a burst period of between about 0.1 and about 10 seconds.

EXAMPLE 1

The Power SNR approach for PMF signal configuration has been tested experimentally on calcium dependent myosin phosphorylation in a standard enzyme assay. The cell-free reaction mixture was chosen for phosphorylation rate to be linear in time for several minutes, and for sub-saturation $Ca^{2+}$ concentration. This opens the biological window for $Ca^{2+}$/CaM to be EMF-sensitive. This system is not responsive to PMF at levels utilized in this study if $Ca^{2+}$ is at saturation levels with respect to CaM, and reaction is not slowed to a minute time range. Experiments were performed using myosin light chain ("MLC") and myosin light chain kinase ("MLCK") isolated from turkey gizzard. A reaction mixture consisted of a basic solution containing 40 mM Hepes buffer, pH 7.0; 0.5 mM magnesium acetate; 1 mg/ml bovine serum albumin, 0.1% (w/v) Tween80; and 1 mM EGTA12. Free $Ca^{2+}$ was varied in the 1-7 µM range. Once $Ca^{2+}$ buffering was established, freshly prepared 70 nM CaM, 160 nM MLC and 2 nM MLCK were added to the basic solution to form a final reaction mixture. The low MLC/MLCK ratio allowed linear time behavior in the minute time range. This provided reproducible enzyme activities and minimized pipetting time errors.

The reaction mixture was freshly prepared daily for each series of experiments and was aliquoted in 100 µL portions into 1.5 ml Eppendorf tubes. All Eppendorf tubes containing reaction mixture were kept at 0° C. then transferred to a specially designed water bath maintained at 37±0.1° C. by constant perfusion of water prewarmed by passage through a Fisher Scientific model 900 heat exchanger. Temperature was monitored with a thermistor probe such as a Cole-Parmer model 8110-20, immersed in one Eppendorf tube during all experiments. Reaction was initiated with 2.5 µM 32P ATP, and was stopped with Laemmli Sample Buffer solution containing 30 µM EDTA. A minimum of five blank samples were counted in each experiment. Blanks comprised a total assay mixture minus one of the active components $Ca^{2+}$, CaM, MLC or MLCK. Experiments for which blank counts were higher than 300 cpm were rejected. Phosphorylation was allowed to proceed for 5 min and was evaluated by counting 32P incorporated in MLC using a TM Analytic model 5303 Mark V liquid scintillation counter.

The signal comprised repetitive bursts of a high frequency waveform. Amplitude was maintained constant at 0.2 G and repetition rate was 1 burst/sec for all exposures. Burst duration varied from 65 µsec to 1000 µsec based upon projections of Power SNR analysis which showed that optimal Power SNR would be achieved as burst duration approached 500 µsec. The results are shown in FIG. 7 wherein burst width 701 in µsec is plotted on the x-axis and Myosin Phosphorylation 702 as treated/sham is plotted on the y-axis. It can be seen that the PMF effect on $Ca^{2+}$ binding to CaM approaches its maximum at approximately 500 µsec, just as illustrated by the Power SNR model.

These results confirm that a PMF signal, configured according to an embodiment of the present invention, would maximally increase myosin phosphorylation for burst durations sufficient to achieve optimal Power SNR for a given magnetic field amplitude.

EXAMPLE 2

According to an embodiment of the present invention use of a Power SNR model was further verified in an in vivo wound repair model. A rat wound model has been well characterized both biomechanically and biochemically, and was used in this study. Healthy, young adult male Sprague Dawley rats weighing more than 300 grams were utilized.

The animals were anesthetized with an intraperitoneal dose of Ketamine 75 mg/kg and Medetomidine 0.5 mg/kg. After adequate anesthesia had been achieved, the dorsum was shaved, prepped with a dilute betadine/alcohol solution, and draped using sterile technique. Using a #10 scalpel, an 8-cm linear incision was performed through the skin down to the fascia on the dorsum of each rat. The wound edges were bluntly dissected to break any remaining dermal fibers, leaving an open wound approximately 4 cm in diameter. Hemostasis was obtained with applied pressure to avoid any damage to the skin edges. The skin edges were then closed with a 4-0 Ethilon running suture. Post-operatively, the animals received Buprenorphine 0.1-0.5 mg/kg, intraperitoneal. They were placed in individual cages and received food and water ad libitum.

PMF exposure comprised two pulsed radio frequency waveforms. The first was a standard clinical PRF signal comprising a 65 µsec burst of 27.12 MHz sinusoidal waves at 1 Gauss amplitude and repeating at 600 bursts/sec. The second was a PRF signal reconfigured according to an embodiment of the present invention. For this signal burst duration was increased to 2000 µsec and the amplitude and repetition rate were reduced to 0.2 G and 5 bursts/sec respectively. PRF was applied for 30 minutes twice daily.

Tensile strength was performed immediately after wound excision. Two 1 cm width strips of skin were transected perpendicular to the scar from each sample and used to measure the tensile strength in $kg/mm^2$. The strips were excised from the same area in each rat to assure consistency of measurement. The strips were then mounted on a tensiometer. The strips were loaded at 10 mm/min and the maximum force generated before the wound pulled apart was recorded. The final tensile strength for comparison was determined by taking the average of the maximum load in kilograms per $mm^2$ of the two strips from the same wound.

The results showed average tensile strength for the 65 µsec 1 Gauss PRF signal was 19.3±4.3 $kg/mm^2$ for the exposed group versus 13.0±3.5 $kg/mm^2$ for the control group ($p<0.01$), which is a 48% increase. In contrast, the average tensile strength for the 2000 µsec 0.2 Gauss PRF signal, configured according to an embodiment of the present invention using a Power SNR model was 21.2±5.6 $kg/mm^2$ for the treated group versus 13.7±4.1 $kg/mm^2$ ($p<0.01$) for the control group, which is a 54% increase. The results for the two signals were not significantly different from each other.

These results demonstrate that an embodiment of the present invention allowed a new PRF signal to be configured that could be produced with significantly lower power. The PRF signal configured according to an embodiment of the present invention, accelerated wound repair in the rat model in a low power manner versus that for a clinical PRF signal which accelerated wound repair but required more than two orders of magnitude more power to produce.

EXAMPLE 3

In this example Jurkat cells react to PMF stimulation of a T-cell receptor with cell cycle arrest and thus behave like normal T-lymphocytes stimulated by antigens at the T-cell receptor such as anti-CD3. For example in bone healing, results have shown both 60 Hz and PEMF fields decrease DNA synthesis of Jurkat cells, as is expected since PMF interacts with the T-cell receptor in the absence of a costimulatory signal. This is consistent with an anti-inflammatory response, as has been observed in clinical applications of PMF stimuli. The PEMF signal is more effective. A dosimetry analysis performed according to an embodiment of the present invention demonstrates why both signals are effective and why PEMF signals have a greater effect than 60 Hz signals on Jurkat cells in the most EMF-sensitive growth stage.

Comparison of dosimetry from the two signals employed involves evaluation of the ratio of the Power spectrum of the thermal noise voltage that is Power SNR, to that of the induced voltage at the EMF-sensitive target pathway structure. The target pathway structure used is ion binding at receptor sites on Jurkat cells suspended in 2 mm of culture medium. The average peak electric field at the binding site from a PEMF signal comprising 5 msec burst of 200 µsec pulses repeating at 15/sec, was 1 mV/cm, while for a 60 Hz signal it was 50 µV/cm.

EXAMPLE 4

In this example electromagnetic field energy was used to stimulate neovascularization in an in vivo model. Two different signal were employed, one configured according to prior art and a second configured according to an embodiment of the present invention.

One hundred and eight Sprague-Dawley male rats weighing approximately 300 grams each, were equally divided into nine groups. All animals were anesthetized with a mixture of ketamine/acepromazine/Stadol at 0.1 cc/g. Using sterile surgical techniques, each animal had a 12 cm to 14 cm segment of tail artery harvested using microsurgical technique. The artery was flushed with 60 U/ml of heparinized saline to remove any blood or emboli. These tail vessels, with an average diameter of 0.4 mm to 0.5 mm, were then sutured to the transected proximal and distal segments of the right femoral artery using two end-to-end anastomoses, creating a femoral arterial loop. The resulting loop was then placed in a subcutaneous pocket created over the animal's abdominal wall/groin musculature, and the groin incision was closed with 4-0 Ethilon. Each animal was then randomly placed into one of nine groups: groups 1 to 3 (controls), these rats received no electromagnetic field treatments and were killed at 4, 8, and 12 weeks; groups 4 to 6, 30 min. treatments twice a day using 0.1 gauss electromagnetic fields for 4, 8, and 12 weeks (animals were killed at 4, 8, and 12 weeks, respectively); and groups 7 to 9, 30 min. treatments twice a day using 2.0 gauss electromagnetic fields for 4, 8, and 12 weeks (animals were killed at 4, 8, and 12 weeks, respectively).

Pulsed electromagnetic energy was applied to the treated groups using a device constructed according to an embodiment of the present invention. Animals in the experimental groups were treated for 30 minutes twice a day at either 0.1 gauss or 2.0 gauss, using short pulses (2 msec to 20 msec) 27.12 MHz. Animals were positioned on top of the applicator head and confined to ensure that treatment was properly applied. The rats were reanesthetized with ketamine/acepromazine/Stadol intraperitoneally and 100 U/kg of heparin intravenously. Using the previous groin incision, the femoral artery was identified and checked for patency. The femoral/tail artery loop was then isolated proximally and distally from the anastomoses sites, and the vessel was clamped off. Animals were then killed. The loop was injected with saline followed by 0.5 cc to 1.0 cc of colored latex through a 25-gauge cannula and clamped. The overlying abdominal skin was carefully resected, and the arterial loop was exposed. Neovascularization was quantified by measuring the surface area covered by new blood-vessel formation delineated by the intraluminal latex. All results were analyzed using the SPSS statistical analysis package.

The most noticeable difference in neovascularization between treated versus untreated rats occurred at week 4. At that time, no new vessel formation was found among controls, however, each of the treated groups had similar statistically significant evidence of neovascularization at 0 cm2 versus 1.42±0.80 cm2 (p<0.001). These areas appeared as a latex blush segmentally distributed along the sides of the arterial loop. At 8 weeks, controls began to demonstrate neovascularization measured at 0.7±0.82 cm2. Both treated groups at 8 weeks again had approximately equal statistically significant (p<0.001) outcroppings of blood vessels of 3.57±1.82 cm2 for the 0.1 gauss group and of 3.77±1.82 cm2 for the 2.0 gauss group. At 12 weeks, animals in the control group displayed 1.75±0.95 cm2 of neovascularization, whereas the 0.1 gauss group demonstrated 5.95±3.25 cm2, and the 2.0 gauss group showed 6.20±3.95 cm2 of arborizing vessels. Again, both treated groups displayed comparable statistically significant findings (p<0.001) over controls.

These experimental findings demonstrate that electromagnetic field stimulation of an isolated arterial loop according to an embodiment of the present invention increases the amount of quantifiable neovascularization in an in vivo rat model. Increased angiogenesis was demonstrated in each of the treated groups at each of the sacrifice dates. No differences were found between the results of the two gauss levels tested as predicted by the teachings of the present invention.

Having described embodiments for an apparatus and a method for delivering electromagnetic treatment to human, animal and plant molecules, cells, tissue and organs, it is noted that modifications and variations can be made by persons skilled in the art in light of the above teachings. It is therefore to be understood that changes may be made in the particular embodiments of the invention disclosed which are within the scope and spirit of the invention as defined by the appended claims.

What is claimed is:

1. A method for electromagnetic treatment of living tissues and cells by enhancing angiogenesis and neovascularization comprising the steps of:

applying a portable electromagnetic treatment device adjacent to a target tissue site;

generating an electromagnetic signal from at least one waveform; and coupling said electromagnetic signal to said angiogenesis and neovascularization target pathway structure using a coupling device; and inducing an electromagnetic field at the target tissue site from the at least one waveform, wherein said at least one waveform is configured to be coupled to an angiogenesis and neovascularization target pathway structure at the target tissue site by modulating binding of calcium to Calmodulin, wherein the waveform induces a power that is greater than the thermal noise power of calcium binding to Calmodulin so that the at least one waveform is configured to be detectable in said angiogenesis and neovascularization target pathway structure above background activity in said angiogenesis and neovascularization target pathway structure.

2. The method of claim 1, wherein said at least one waveform comprises at least one of a frequency component parameter that configures said at least one waveform to repeat between about 0.01 Hz and about 100 MHz, a burst amplitude envelope parameter that follows a mathematically defined amplitude function, a burst width parameter that varies at each repetition according to a mathematically defined width function, a peak induced electric field parameter varying between about 1 µV/cm and about 100 mV/cm in said target pathway structure according to a mathematically defined function, and a peak induced magnetic field parameter varying between about 1 and about 0.1 T in said target pathway structure according to a mathematically defined function.

3. The method of claim 1, wherein said angiogenesis and neovascularization target pathway structure includes the binding of at least one of ions and ligands.

4. The method of claim 1, wherein said inducing an electromagnetic field at the target tissue site comprises modulating growth factor production in living cells and tissues.

5. The method of claim 1, wherein said inducing an electromagnetic field at the target tissue site comprises modulating cytokine production in living cells and tissues.

6. The method of claim 1, wherein said inducing an electromagnetic field at the target tissue site comprises modulating growth factors and cytokines relevant to angiogenesis and neovascularization.

7. The method of claim 1, wherein said inducing an electromagnetic field at the target tissue site comprises modulating angiogenesis and neovascularization for treatment of bone fractures and disorders.

8. The method of claim 1, wherein said inducing an electromagnetic field at the target tissue site comprises modulating angiogenesis and neovascularization for treatment of cardiovascular diseases.

9. The method of claim 1, wherein said inducing an electromagnetic field at the target tissue site comprises modulating angiogenesis and neovascularization for treatment of cerebral diseases.

10. The method of claim 1, wherein said inducing an electromagnetic field at the target tissue site comprises modulating angiogenesis and neovascularization for treatment of cerebrovascular disease.

11. The method of claim 1, wherein said inducing an electromagnetic field at the target tissue site comprises modulating angiogenesis and neovascularization for treatment peripheral vascular disease.

12. The method of claim 1, wherein said inducing an electromagnetic field at the target tissue site comprises modulating angiogenesis and neovascularization for treatment of diseased or ischemic cells and tissues.

13. The method of claim 1, wherein said inducing an electromagnetic field at the target tissue site comprises modulating angiogenesis and neovascularization for treatment of an acute or chronic soft tissue wound.

14. The method of claim 1, wherein said inducing an electromagnetic field at the target tissue site comprises modulating angiogenesis and neovascularization for treatment of sprains strains and contusions.

15. The method of claim 1, wherein the at least one waveform comprises frequency components for coupling to an impedance of the binding of calcium to Calmodulin and thus the angiogenesis and neovascularization target pathway.

16. The method of claim 15, wherein the at least one waveform comprises frequency components that fall within the bandpass of the kinetics of binding of calcium to Calmodulin.

17. The method of claim 1, wherein generating the electromagnetic signal comprises generating a burst of arbitrary waveforms having a plurality of frequency components ranging from about 0.01Hz to about 100 MHz, the plurality of frequency components satisfying a SNR or PSNR model for the angiogenesis and neovascularization target pathway structure.

18. The method of claim 1, wherein the induced electromagnetic field comprises a burst duration between about 10 msec to about 100 msec.

19. The method of claim 1, wherein the induced electromagnetic field comprises a peak amplitude between about 1 µV/cm and about 100 mV/cm.

20. The method of claim 1, wherein the at least one waveform has a frequency of approximately 27.12 MHz.

21. The method of claim 1, wherein generating the electromagnetic signal comprises applying a treatment regime so that the electromagnetic signal is applied according to the treatment regimen.

22. The method of claim 21, wherein the treatment regimen applies the electromagnetic signal for a total time of under 1 minute to 240 minutes daily.

23. The method of claim 1, wherein the electromagnetic signal comprises a duty cycle of between about 1 to about $10^{-5}$.

24. A method for electromagnetic treatment of living tissues and cells by enhancing angiogenesis and neovascularization comprising the steps of:
    applying a portable electromagnetic treatment device adjacent to a target tissue site;
    generating an electromagnetic signal from at least one waveform; and
    coupling said electromagnetic signal to said angiogenesis and neovascularization target pathway structure using a coupling device; and
    inducing an electromagnetic field at the target tissue site from the at least one waveform, wherein said at least one waveform is configured to be coupled to an angiogenesis and neovascularization target pathway structure at the target tissue site, wherein the waveform is further configured to have a time constant that matches the bandpass of calcium binding to Calmodulin according to an electrically equivalent model of calcium binding to Calmodulin, and wherein the waveform is configured to induce a power at the target tissue that is greater than the thermal noise power of calcium binding to Calmodulin.

* * * * *